(12) United States Patent
Devarajan et al.

(10) Patent No.: US 9,880,165 B2
(45) Date of Patent: Jan. 30, 2018

(54) DETECTION OF WORSENING RENAL DISEASE IN SUBJECTS WITH SYSTEMIC LUPUS ERYTHEMATOSUS

(75) Inventors: Prasad Devarajan, Cincinnati, OH (US); Hermine I. Brunner, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 780 days.

(21) Appl. No.: 12/770,915

(22) Filed: Apr. 30, 2010

(65) Prior Publication Data

US 2010/0323911 A1     Dec. 23, 2010

Related U.S. Application Data

(63) Continuation-in-part of application No. PCT/US2008/082166, filed on Oct. 31, 2008.

(60) Provisional application No. 60/984,233, filed on Oct. 31, 2007.

(51) Int. Cl.
*C40B 30/04* (2006.01)
*G01N 33/53* (2006.01)
*G01N 33/564* (2006.01)

(52) U.S. Cl.
CPC ....... *G01N 33/564* (2013.01); *G01N 2800/24* (2013.01)

(58) Field of Classification Search
None
See application file for complete search history.

(56) References Cited

U.S. PATENT DOCUMENTS

| 4,812,397 | A | 3/1989 | Weisbart |
|---|---|---|---|
| 7,037,651 | B2 | 5/2006 | Tsao et al. |
| 2003/0198959 | A1 | 10/2003 | Kurnit |
| 2004/0219603 | A1 | 11/2004 | Devarajan et al. |
| 2005/0191664 | A1 | 9/2005 | Comper |
| 2005/0272101 | A1 | 12/2005 | Devarajan et al. |
| 2007/0037232 | A1 | 2/2007 | Barasch et al. |
| 2008/0274118 | A1 | 11/2008 | Aukerman et al. |
| 2009/0170143 | A1 | 7/2009 | Uttenthal et al. |
| 2010/0015648 | A1 | 1/2010 | Barasch et al. |

FOREIGN PATENT DOCUMENTS

| WO | WO 2006/135775 A2 | 12/2006 |
|---|---|---|
| WO | WO 2007/070376 A2 | 6/2007 |

OTHER PUBLICATIONS

Tay et al. Selectivity of Proteinuria in Nephrotic Syndrome. Aug. 1971. Singapore Medical Journal. vol. 12, No. 4, pp. 233-236.*

Suzuki et al. Initial Validation of a Novel Protein Biomarker Panel for Active Pediatric Lupus Nephritis. Pediatric Research. May 2009. vol. 65, No. 5, pp. 530-536.*
U.S. Appl. No. 10/811,130, filed Mar. 26, 2004, Devarajan, Prasad, et al.
U.S. Appl. No. 10/096,113, filed Mar. 31, 2005, Devarajan, Prasad, et al.
U.S. Appl. No. 12/567,860, filed Sep. 28, 2009, Barasch, Jonathan Matthew, et al.
Brunner, H.I. et al. "Urinary Neutrophil Gelatinase-Associated Lipocalin as a Biomarker of Nephritis in Childhood-Onset Systemic Lupus Erythematosus." 2006: E-published on Jul. 25, 2006. Arthritis & Rheumatism, vol. 54, No. 8, Aug. 2006, pp. 2577-2584.
Bolignano, D. et al. "Urinary Neutrophil Gelatinase-Associated Lipocalin (NGAL) is associated with severity of renal disease in proteinuric patients." 2007: F.-published by NDT Advance Access on Sep. 24, 2007. Nephrol Dial Transplant, 2008, vol. 23(1), pp. 414-416.
Denko, C.W. et al. "Serum proteins—transferrin, ceruloplasmin, albumin, alpha 1-acid glycoprotein, alpha 1-antitrypsin—in rheumatic disorders." J. Rheumatol. Nov.-Dec. 1979; vol. 6(6): pp. 664-672.
Devarajan, P. et al. "Proteomics for Biomarker Discovery in Acute Kidney Injury." Semin. Nephrol. Nov. 2007; vol. 27(6): pp. 637-651.
Houssiau, F.A. et al. "Lupus nephritis: the significance of serological tests at the time of biopsy." Clin Exp Rheumatol., Jul.-Aug. 1991; vol. 9(4): pp. 345-349.
Joachim, G.R. et al. "Selectivity of Protein Excretion in Patients with the Nephrotic Syndrome." J. of Clin. Invest., vol. 43, No. 12, 1964, pp. 2332-2346.
Mackiewicz, A. et al. "Glycoforms of serum α1-acid glycoprotein as markers of inflammation and cancer." Glycoconj J., Jun. 1995; vol. 12(3): 241-247.
Mackiewicz, A. et al. "Microheterogeneity of Alpha$_1$-Acid Glycoprotein in the Detection of Intercurrent Infection in Systemic Lupus Erythematosus." Arthritis Rheum., May 1987; vol. 30(5): pp. 513-518.
Meijer, C. et al. "Profiles of Cytokines (TNF alpha and IL-6) and Acute Phase Proteins (CRP and Alpha IAG) related to the Disease Course in Patients with Systemic Lupus Erythematosus." Lupus, Dec. 1993, vol. 2(6): pp. 359-365.
Oates, J.C. et al. "Prediction of urinary protein markers in lupus nephritis." Kidney Int., Dec. 2005; vol. 68(6): 2588-2592.
Pitashny, M. et al. "Urinary Lipocalin-2 is Associated with Renal Disease Activity in Human Lupus Nephritis." Arthritis & Rheumatism, Jun. 2007, vol. 56(6): pp. 1894-1903.
Suzuki, M. et al. "Neutrophil gelatinase-associated lipocalin as a biomarker of disease activity in pediatric lupus nephritis." Pediatr Nephrol, Mar. 2008, vol. 23(3): pp. 403-412.
Suzuki, M. et al. "Identification of a urinary proteomic signature for lupus nephritis in children." Pediatr Nephrol., Dec. 2007, vol. 22(12), pp. 2047-2057.

(Continued)

*Primary Examiner* — Channing S Mahatan
(74) *Attorney, Agent, or Firm* — Frost Brown Todd LLC

(57) ABSTRACT

Methods for the detection of active lupus nephritis (LN) and worsening renal disease activity and/or active LN in patients diagnosed with systemic lupus erythematosus, using a panel of biomarkers including transferrin (Tf), ceruloplasmin (Cp), alpha-1-acid glycoprotein (AGP1), lipocalin-like prostaglandin D synthetase (L-PGDS), and urinary neutrophil gelatinase associated lipocalin (UNGAL).

9 Claims, 6 Drawing Sheets

(56) References Cited

OTHER PUBLICATIONS

Swaak, A.J.G. et al. "Interleukin-6 (IL-6) and acute phase proteins in the disease course of patients with systemic lupus erythematosus." Rheumatol Int. 1989; vol. 8(6): pp. 263-268.

Taysi, S. et al. "Serum oxidant/antioxidant status of patients with systemic lupus erythematosus." Clin. Chem. Lab Med., Jul. 2002; vol. 40(7): pp. 684-688.

Terai, C. et al. "Determination of urinary albumin excretion by radioimmunoassay in patients with subclinical lupus nephritis." Clin Nephrol., Feb. 1987; vol. 27, No. 2: pp. 79-83.

Tian, S. et al. "Urinary levels of RANTES and M-CSF are predictors of lupus nephritis flare." Inflamm. Res., 2007, vol. 56, pp. 304-310.

Varghese, S.A. et al. "Urine Biomarkers Predict the Cause of Glomerular Disease." J. Am. Soc. Nephrol., Mar. 2007; vol. 18(3): pp. 913-922.

Yilmaz, A. et al. "Trace elements and some extracellular antioxidant proteins levels in serum of patients with systemic lupus erythematosus." Clin. Rheumatol., (2005), vol. 24: pp. 331-335.

Zappitelli, M. et al. "Urine neutrophil gelatinase-associated lipocalin is an early marker of acute kidney injury in critically ill children: a prospective cohort study." Critical Care, Aug. 2, 2007; vol. 11(4) No. 4 R84.

Zhuang, X-H et al. "Analysis of renal impairment in children with Wilson's disease." World J Pediatr, May 15, 2008; vol. 4, No. 2, pp. 102-105.

Schiffenbauer, J., et al, "Biomarkers, Surrogate Markers, and Design of Clinical Trials of New Therapies for Systemic Lupus Erythematosus," Arthritis & Rheumatism, Aug. 2004, pp. 2415-2422, vol. 50, No. 8, American College of Rheumatology.

* cited by examiner

DETECTION OF WORSENING RENAL DISEASE IN SUBJECTS WITH SYSTEMIC LUPUS ERYTHEMATOSUS

CROSS REFERENCE TO RELATED APPLICATIONS

This application is a continuation-in-part of International Application PCT/US2008/082166, with an international filing date of Oct. 31, 2008, which claimed the benefit of U.S. Provisional Application No. 60/984,233, filed Oct. 31, 2007.

FIELD OF THE INVENTION

The present invention relates generally to the treatment of systemic lupus erythematosus (SLE), and in particular to a method and kit for the early determination of active Lupus nephritis or worsening renal disease activity in a patient suffering from SLE.

BACKGROUND OF THE INVENTION

Early detection of disease states in mammals has been the focus of much recent research. For disease detection, the public-health community has historically relied on laboratory tests that can sometimes take days or even weeks to return a result. The increased availability of better and faster diagnostic tests, however, promises the possibility of more automated and earlier disease detection and subsequent intervention. Early detection of disease can lead to introduction of therapy early in the disease process, as well as to improved therapy methods.

Systemic lupus erythematosus (also called SLE, or lupus) is a chronic inflammatory autoimmune disease that can affect any organ or organ system. The presence of auto-antibodies, especially those directed to double-stranded DNA, is characteristic for the disease. Sometimes called the "great imitator" because its widely varied symptoms are often mistaken for other disorders, SLE has the potential to affect the skin, joints, kidneys, lungs, nervous system, and/or other organs of the body. The most common symptoms of SLE include skin rashes and arthritis, often accompanied by fatigue and fever. Although SLE can be a fatal disease, the clinical course typically varies from mild to severe, and involves alternating periods of remission and relapse.

Among the principal determinants of poor prognosis in SLE is a severe and progressive renal involvement known as lupus nephritis (LN), a complication more frequently encountered in children than adults with the disease. LN is a complication of SLE related to the autoimmune process of SLE, where complexes of antinuclear antibodies and complement accumulate in the kidneys and result in an inflammatory response. LN typically manifests as mild proteinuria, hematuria, azotemia, hypertension, or urine sediment consisting of red blood cell casts, waxy casts, and cellular debris, or any combination of these. However, LN can also manifest as a rapidly progressive glomerulonephritis. Almost every patient with LN has proteinuria, with 45% to 65% of these patients developing the nephrotic syndrome. LN occurs in approximately 50% of patients with SLE within 1 year of diagnosis, and 15% to 20% of these patients develop renal disease severe enough to require renal replacement therapy.

Renal involvement (including worsening renal disease activity and/or LN) is one of the main determinants of poor prognosis of SLE, and is more frequently encountered in children (cSLE) than adults with SLE. Typically, increased disease activity in SLE patients typically cannot be determined by a single laboratory value or clinical sign. For example, proteinuria can be a sign of active LN, but also occurs with renal damage of any cause. While laboratory tests such as BUN, serum creatinine, proteinuria, etc. may help in the diagnosis of worsening SLE renal disease activity, currently available renal biomarkers, e.g. measures of the degree of SLE renal disease activity and severity, are too insensitive and non-specific to allow for the early identification and diagnosis of active SLE nephritis. Further, randomized clinical trials in SLE are hindered by the lack of high-quality biomarkers to allow timely therapy to avoid permanent renal damage or to verify the effects of therapies within a short period of time.

Definitive diagnosis of SLE renal disease is currently established on the basis of a combination of clinical, laboratory, and pathologic findings, and often requires a renal biopsy. Three of these validated measures are the Systemic Lupus Erythematosus Disease Activity Index (SLEDAI), the British Isles Lupus Assessment Group index (BILAG), and the Systemic Lupus Activity Measure (SLAM). They have been accepted for use in assessing both adults and children with SLE. However, the SLEDAI may be preferable overall.

Because there is no uniquely accepted way to determine worsening disease activity in SLE, the quest for a reliable early biomarker of active LN and/or lupus nephritis caused by SLE is an area of intense contemporary research. An improved method for the early detection of active LN in patients with SLE could lead to improvements in therapy, and could significantly increase life expectancy and quality of life.

SUMMARY OF THE INVENTION

According to the methods of the present invention, a protein signature or "Lupus Nephritis Panel" for identifying worsening renal disease activity and/or active lupus nephritis (LN) caused by SLE is provided, consisting of four renal biomarkers: transferrin (Tf), ceruloplasmin (Cp), lipocalin-type prostaglandin-D synthetase (L-PGDS), and alpha-1-acid-glycoprotein (AGP). A fifth biomarker, neutrophil gelatinase associated lipocalin (NGAL), while known generally as a biomarker for determining renal failure and disease of many chronic and acute causes, can also be included in this panel if limited to the form of urinary NGAL (UNGAL). This panel of biomarkers can be used for the accurate diagnosis and determination of the course of lupus nephritis in both children and adults with SLE. While each individual biomarker can be used alone, the combination of two or more of these biomarkers can improve the diagnostic capability. Additionally, these urinary biomarkers can be used to determine whether WHO Class 4 or Class 5 lupus nephritis is present by simple urine testing, in an effort to help tailor medication regimens and follow response to therapy.

One aspect of the present invention provides a method for diagnosing active lupus nephritis (LN) in a mammalian subject diagnosed with systemic lupus erythematosus (SLE), the method comprising the steps of: (a) performing an assay on an initial urine sample obtained from the subject, wherein the assay detects a quantity of at least one biomarker of active LN, wherein the biomarker of active LN is selected from the group consisting of transferrin (Tf), ceruloplasmin (Cp), alpha-1-acid-glycoprotein (AGP), lipocalin-type prostaglandin-D synthetase (L-PGDS), and combinations thereof; and (b) diagnosing the subject with active LN if the quantity is elevated above a predetermined cutoff value for the detected biomarker of LN, and with stable renal disease activity if the quantity is substantially equal to the predetermined cutoff value for the detected biomarker of LN.

The method can further predict flare-ups of active LN. This can be done by performing the assay on a second urine sample obtained from a subject diagnosed with active LN, such that the measurement of significantly increased urinary levels of at least one of the biomarkers of LN predict that the subject is prone to developing a worsening active LN. With this method, the second urine sample can be obtained within a period of time after the time of obtaining the first sample up to and including 12 months, or up to and including 9 months, or up to and including 6 months, or up to and including 4 months, or up to and including 3 months, or up to and including 2 months, or up to and including 6 weeks, or up to and including 4 weeks, or up to and including 3 weeks, or up to and including 2 weeks, or up to and including 1 week.

Another aspect of the invention provides a method for determination of the degree of renal disease activity in a mammalian subject diagnosed with systemic lupus erythematosus (SLE), the method comprising the steps of: (a) performing a baseline assay on a baseline urine sample obtained from a mammalian subject diagnosed with systemic lupus erythematosus, wherein the baseline assay detects a baseline quantity of a biomarker of worsening renal disease activity; (b) performing a second assay on a second urine sample obtained from the subject, wherein the second assay detects a second quantity of the biomarker of worsening renal disease activity; (c) comparing the baseline quantity with the second quantity; and (d) diagnosing the subject with worsening renal disease activity if the second quantity is greater than the baseline quantity, with improved renal disease activity if the second quantity is less than the baseline quantity, and with unchanged renal disease activity if the second quantity is substantially equal to the baseline quantity. Typically the biomarker of worsening renal disease activity is selected from the group consisting of transferrin, ceruloplasmin, lipocalin-like prostaglandin D synthetase, alpha-1-acid glycoprotein, and combinations thereof.

Another aspect of the invention provides a method for determining the response to therapy in a mammalian subject being treated for lupus nephritis (LN) resulting from systemic lupus erythematosus (SLE), the method comprising the steps of: (a) performing a first assay on a first urine sample obtained from a mammalian subject with SLE, wherein the first assay detects a first quantity of a biomarker of LN, the biomarker selected from the group consisting of transferrin, ceruloplasmin, lipocalin-like prostaglandin D synthetase, alpha-1-acid glycoprotein, and combinations thereof; (b) diagnosing the subject with LN based at least in part on the first quantity; (c) managing subject treatment based on the diagnosis of LN; (d) performing a second assay on a second urine sample obtained from the subject after managing subject treatment, wherein the second assay detects a second quantity of the biomarker of LN; and (e) determining that LN activity in the subject has changed subsequent to managing subject treatment, based on the comparison of the first quantity with the second quantity.

Another aspect of the invention provides a method of diagnosing, monitoring or determining the likelihood of lupus nephritis (LN) in a human being diagnosed with systemic lupus erythematosus (SLE), wherein the method discriminates between lupus nephritis and a renal disorder that is not caused by lupus nephritis, said method comprising the steps of: (a) determining the concentration of a biomarker of worsening renal disease activity in a urine sample obtained from a mammalian subject diagnosed with SLE, the biomarker selected from the group consisting of transferrin, ceruloplasmin, lipocalin-like prostaglandin D synthetase, alpha-1-acid glycoprotein, and combinations thereof; and (b) comparing the concentration of the biomarker with a predetermined cutoff value, the cutoff value being chosen to exclude lower concentrations of the biomarker associated with conditions that are not related to SLE, wherein a concentration above the cutoff value is indicative of lupus nephritis.

Another aspect of the invention is a method for determining that a mammalian subject having active lupus nephritis (LN), has or is prone to developing a worsening active LN, comprising the steps of: a) performing an assay on a first urine sample, obtained from a mammalian subject diagnosed with active LN, that detects a first level of a biomarker for active LN, consisting of neutrophil gelatinase-associated lipocalin (NGAL); b) performing the assay on a second urine sample obtained from the mammalian subject, that detects a second level of NGAL; and c) correlating an elevated second level of NGAL, compared to the first level of NGAL, to the mammalian subject having a worsening active LN.

The invention provides that a first level of NGAL that is at least 5 ng/ml urine, or at least 10 ng/ml urine, and up to 20 ng/ml urine, or up to 15 ng/ml urine. It is understood that the detected level of NGAL may be affected by any one or more of, sampling error, normal variation in the assay, the type of assay, the type of antibodies employed, and others. Typically, the first level of NGAL is higher than a predetermined level of NGAL in urine from normal, healthy subjects, by an amount of at least 5 ng/ml urine, or at least 10 ng/ml urine, or at least 15 ng/ml urine. Typically, the first level of NGAL is at least 50% higher than the predetermined level of NGAL in the urine of normal, healthy subjects, or at least 100% higher, or at least 150% higher, or at least 200% higher, or at least 300% higher.

Another aspect of the invention is a method for determining that a mammalian subject having active lupus nephritis (LN), likely to experience to a renal flare, comprising the steps of: a) performing an assay on a urine sample, obtained from a mammalian subject diagnosed with active LN, that detects a level of a biomarker for active LN, consisting of neutrophil gelatinase-associated lipocalin (NGAL); and b) correlating the elevated level of NGAL to the mammalian subject being likely to experiencing a renal flare. The elevated level of NGAL of at least 15 mg NGAL/ml urine, or at least 20 mg NGAL/ml urine, or at least 25 mg NGAL/ml urine, or at least 30 mg NGAL/ml urine, or at least 35 mg NGAL/ml urine, or at least 40 mg NGAL/ml urine. The mammalian subject is likely to experience a renal flare, in that if the renal condition of the mammalian subject is not differently treated, and without additional treatment, an onset of a renal flare is probably and likely to occur. The onset of the renal flare, to which the mammalian subject is likely to experience, can occur within the following 6 months, or within the following 5 months, or within the following 4 months, or within the following 3 months, or within the following 2 months, or within the following 1 month, or within the following 4 weeks, or within the following 3 weeks, or within the following 2 weeks.

The invention provides that an elevated second level of NGAL is higher than the first level of NGAL by at least 5 ng/ml urine, or at least 7 ng/ml urine, or at least 10 ng/ml urine, or at least 15 ng/ml urine, or at least 20 ng/ml urine, or at least 25 ng/ml, or at least 30 ng/ml urine, or at least 35 ng/ml urine, or at least 40 ng/ml urine. The elevated second level of NGAL is typically at least 50% higher than the first level of NGAL, at least 60% higher than the first level of NGAL, at least 70% higher than the first level of NGAL, or at least 80% higher, or at least 90% higher than the first level of NGAL, or at least 100% higher, or at least 150% higher, or at least 200% higher, or at least 300% higher. Typically, the second urine sample is obtained within a period of time after the time of obtaining the first sample, of up to and including 12 months, or up to and including 9 months, or up to and including 6 months, or up to and including 4 months, or up to and including 3 months, or up to and including 2 months, or up to and including 6 weeks, or up to and including 4 weeks, or up to and including 3 weeks, or up to and including 2 weeks, or up to and including 1 week.

The invention also provides for determining the response of the mammalian subject following a treatment for the LN, further comprising the steps of: i) performing the assay on a post-treatment urine sample obtained from the mammalian subject following a treatment for LN, that detects a post-treatment level of NGAL; and ii) comparing the post-treatment level of NGAL to the second level of NGAL, to determine the response to the treatment for the LN.

The invention provides that the post-treatment urine sample is typically obtained within a period of time following the treatment for LN, of up to and including 6 months, or up to and including 4 months, or up to and including 3 months, or up to and including 2 months, or up to and including 6 weeks, or up to and including 4 weeks, or up to and including 3 weeks, or up to and including 2 weeks, or up to and including 1 week, or up to and including 6 days, or up to and including 5 days, or up to and including 4 days, or up to and including 3 days, or up to and including 2 days, or up to and including 24 hours, or up to and including 12 hours or up to and including 9 hours, or up to and including 6 hours, or up to and including 3 hours, or up to and including 2 hours, or up to and including 1 hour.

The invention provides that the step of performing the assay to detect any level of NGAL in a urine sample comprises contacting the urine sample with an antibody for NGAL, to allow formation of a complex of the antibody and the NGAL, and detecting the antibody-NGAL complex, which can include contacting the complex with a second antibody for detecting NGAL.

The urine sample can be a neat, diluted or unprocessed sample, or processed such as by centrifugation or concentration.

Previous studies (Brunner et al, Arthritis & Rheumatism, Vol. 54, No. 8, pp 2577, 2584, 2006, the disclosure of which is incorporated herein by reference) showed that UNGAL is very sensitive and specific for identifying cSLE subjects with biopsy-proven nephritis, active renal disease, and renal damage. UNGAL is a reliable renal biomarker of worsening disease activity and worsening LN, that enable effectively testing for long-term predictive properties of UNGAL that can predict, prognose, and demonstrate the likelihood that a mammalian subject, including human and an adult or child having SLE, will later develop or be diagnosed, by conventional methods, as having worsening LN, in the absence of any intervening care or treatment for active LN.

The present invention provides a method and use for urinary NGAL (NGAL detected in the urine) to predict, up to 6 months, or up to 5 months, or up to 4 months, or up to 3 months, or up to 2 months, the onset or development of worsening LN, as subsequently and eventually shown by conventional diagnostic means. This results from a substantial and/or significant increase or elevation in urinary NGAL up to up to 6 months or any interval therebefore, prior to the subsequent development or worsening of active LN based upon measurement or determination by BILAG renal, MD renal and SLEDAI-2K renal domain scores.

Furthermore, serial or longitudinal measurements of NGAL in the urine, or blood plasma or serum (via assaying of obtained samples), can diagnose and predict an impending worsening of global SLE and LN, respectively, which signals, enables and permits initiation of early treatment of the disease condition. Because urine NGAL increases prior to the occurrence of renal flares, the method is useful for medical decision making to help intercede and abort impending renal flares in patients with SLE.

The nature and advantages of the present invention will be more fully appreciated from the following drawings and detailed description.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

Figure 1:
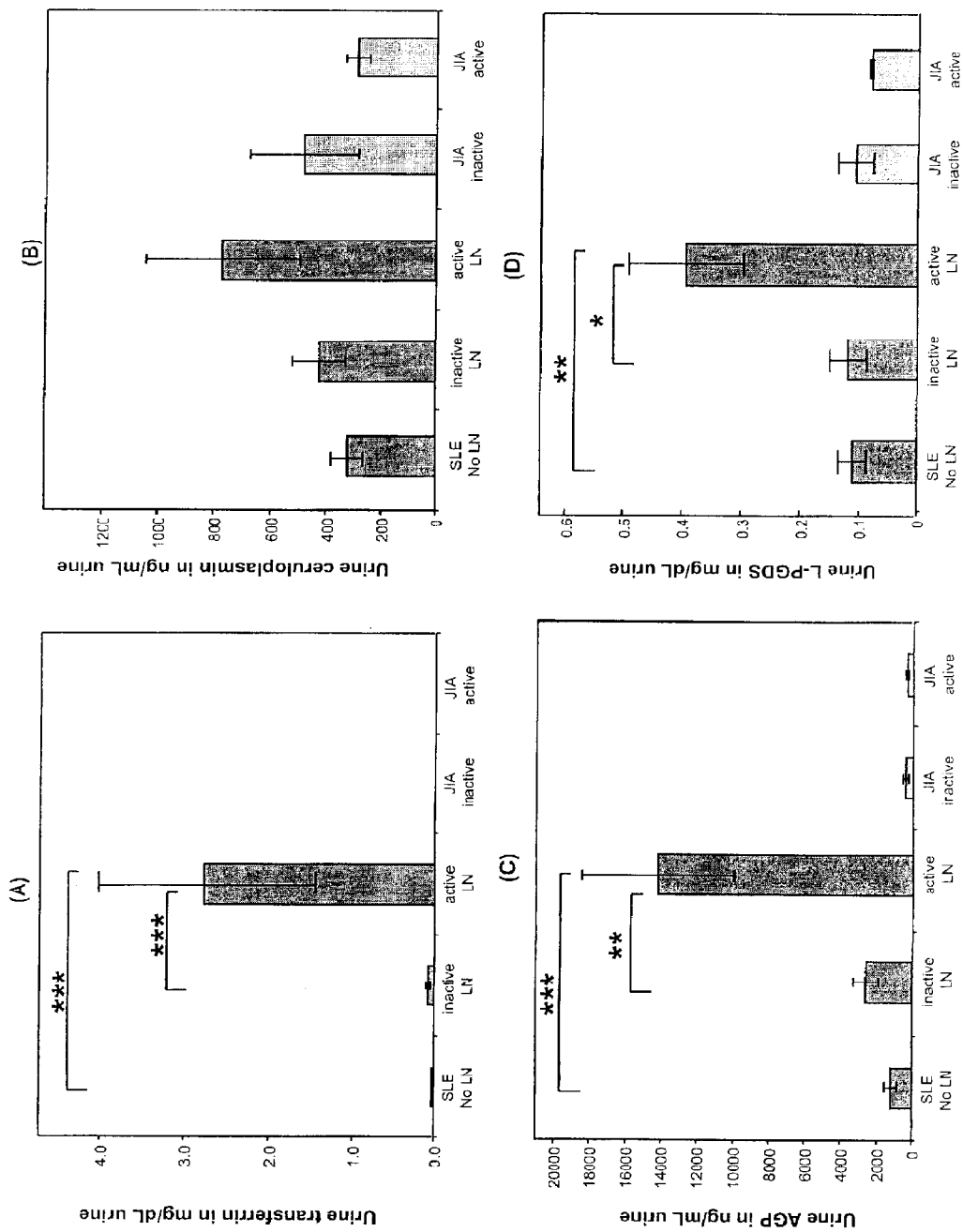
FIG. 1 is a graph showing uncorrected urinary concentrations of the proteins of the LN panel of the invention (per mL or dL of urine). Significant differences between groups are indicated as follows: *=P<0.004; =P<0.002; *=P<0.00001.

The practice of the present invention will employ, unless otherwise indicated, conventional methods of nephrology, molecular biology and other laboratory techniques within the skill of the art. In describing the invention, and as used in this specification and the appended claims, the following terms and phrases will be employed, and are intended to be defined as indicated below. The singular forms "a," "an" and "the" include plural references unless the content clearly dictates otherwise.

As used herein, the term "UNGAL-ml" is, unless otherwise indicated, the amount of urinary NGAL in nanograms (ng) per milliliter (ml) of urine (ng/ml urine).

The term "UNGAL-crea" is, unless otherwise indicated, the amount of urinary NGAL in nanograms per milligram (mg) of urine creatinine (ng/ml urine creatinine), to correct for differences in NGAL due to urine dilution.

The term "PNGAL" is, unless otherwise indicated, the concentration of NGAL in the plasma, blood or serum (ng/ml).

The term "assay" means generally an analysis (including an analysis via SDS PAGE, ELISA, Western Blot) done on a sample to determine the presence of a substance and/or the amount or level of that substance in the sample. Thus, an assay may be done, for example, to determine the level of a biomarker of lupus nephritis in a biological fluid.

The phrase "active lupus nephritis" or "active LN" means a 2 k-version of the Systemic Lupus Erythematosus Disease Activity Index ("SLEDAI-2K") of greater than 0, or a British Isles Lupus Activity Group index ("BILAG") of greater than 1.

The term "biomarker" or "biomarkers" means a molecule or protein that is indicative of a particular pathological state. An effective biomarker of lupus nephritis is typically a secreted protein, whereby it can be excreted by the kidney into the urine or transported within the blood scrum.

The term "flare" or the phrase "renal flare" means a significant increase in inflammation targeting the kidney of a subject already experiencing active lupus nephritis, that can result in a significant, reproducible increase in serum creatinine, proteinuria and/or hematuria, and reduction of renal function.

The phrases "normal, healthy subject" or "healthy control" mean an individual who is not experiencing diminished renal function, such as acute or chronic renal disease, acute renal inflammation, acute infection, or other condition or disease which can increase the level of renal biomarkers in the urine, including Tf, Cp, AGP1, L-PGDS, and UNGAL.

The phrase "improved renal status" means an improvement in renal function, which can be further categorized according to the amount of improvement. For example, in an SLE subject who has received treatment for previously worsening renal disease activity, improved renal status can be classified as slightly improved, moderately improved, and greatly improved, as compared to predetermined levels.

The term "increased amount" or "increased quantity" means an amount or quantity that is greater than or more, as compared to a predetermined amount or quantity or a prior assay amount or quantity.

The term "lupus nephritis" means a kidney disorder that is a complication of systemic lupus erythematosus, characterized by worsening renal disease activity that may include damage to the glomeruli and progressive loss of kidney function.

The phrase "managing subject treatment" refers to the therapy provided or the behavior of a clinician or physician subsequent to the determination of a SLE subject's renal status. As a non-limiting example, if test results are inconclusive or there is reason that confirmation of status is necessary, the physician may order more tests, including one or more additional assays of a sample. Alternatively, if the result indicates that treating for lupus nephritis is appropriate, the physician may schedule the patient for the appropriate treatment. Likewise, if the result is negative (e.g., there is no indication of worsening renal disease activity or lupus nephritis), no further management may be necessary.

The term "Mean+SE" means the mean and standard error.

The term "molecular weight" means, unless otherwise indicated, the average molecular weight in kilodaltons (kDa) of a particular protein or biomarker that is measured, within a margin of error consistent with the measuring system being used. Experimental error and deviation should be allowed for.

The phrase "predetermined level" means (1) a known standard level as it pertains to levels typically found in samples from similar mammalian subjects, including normal, healthy subjects; or (2) a level previously measured in a similar sample(s) from a particular mammalian subject.

The term "renal status" means the condition or state of a subject's renal condition or renal function. Generally the renal status is determined to be normal or impaired condition or function, or improved as compared to a previous impaired condition or function, as determined by diagnostic assessments or assays.

The term "sample" means a sample of a body fluid obtained from a mammalian subject, including urine and blood, and serum and plasma samples derived therefrom.

The phrase "worsening renal disease activity" means worsening renal disease activity, worsening LN, renal flare, or a further decline in renal function, typically in a subject diagnosed with SLE.

The present invention provides methods for the determination of worsening renal disease activity and/or lupus nephritis (LN) in a mammalian subject diagnosed with and/or experiencing systemic lupus erythematosus (SLE). The methods utilize assays for obtaining information on the level of protein expression, or protein expression profiling. Proteins in body fluid samples are defined by their mass-to-charge ratio (m/z), typically according to the SELDI-TOF-MS (surface-enhanced laser desorption/ionization time-of-flight mass spectrometry) proteome analysis technique.

Using these proteomic profiling techniques, the present invention has discovered four new renal biomarkers for assessing features of active lupus nephritis, and that are herein proposed as making up a basic Lupus Nephritis Panel (LN-Panel). These four renal biomarkers of active lupus nephritis are: (1) transferrin (Tf), (2) ceruloplasmin (Cp), (3) lipocalin-like prostaglandin D synthetase (L-PGDS), and (4) alpha-1-acid glycoprotein (AGP1). In addition, a fifth biomarker, urinary neutrophil gelatinase-associated lipocalin (UNGAL), can also be included in this panel. The invention has found that, even after correction for differences in urine:protein creatinine ratio or renal clearance, Tf, Cp, AGP1, L-PGDS, and optionally additionally UNGAL, remain statistically significant predictors of LN activity, irrespective of medication use. Tf, Cp, AGP1, and L-PGDS, which make up the basic LN-Panel of the invention, are effective biomarkers of active LN and are promising renal biomarkers for assessing features of worsening renal disease activity.

Currently, LN is gauged by measuring circulating and excreted indicators of renal dysfunction, with supporting information from kidney biopsies. The latter constitute the current standard for the diagnosis of LN, providing a direct assessment of the presence, severity and activity of LN, and the degree of renal damage. Due to the invasive nature of kidney biopsies, clinicians base LN activity and its therapy on the results of urinary protein excretion, urinary sediment, creatinine clearance and serum albumin. These traditional markers are not accurate in assessing whether active LN is present or not, and none of them is predictive, i.e. able to anticipate the course of LN. Using Surface-Enhanced Laser Desorption/Ionization Time-of-Flight Mass Spectrometry (SELDI-TOF MS) technology, we previously identified a "Lupus Nephritis Panel" consisting of eight candidate biomarkers at the mass-to-charge ratios (m/z) of 2.763, 22, 23, 44, 56, 79, 100, and 133 kDa. In the present invention, we present the identification of the specific proteins contained in this LN-Panel. We further assayed plasma and urine samples of SLE patients and controls with juvenile idiopathic arthritis (JIA) to investigate the concurrent and predictive validity of the proteins to serve as biomarkers of LN activity.

We measured plasma and urinary transferrin (Tf), plasma ceruloplasmin (Cp), plasma α-1-acid-glycoprotein (AGP, also: orosomucoid), as well as plasma and urine lipocalin-type prostaglandin-D synthetase (L-PGDS) by immunonephelometry (Dade Behring BNII Prospect, Marburg, Germany). Urinary Cp was quantified by ELISA (Human Ceruloplasmin ELISA Quantitation Kit; Genway Biotech, Inc., San Diego, Calif., USA); and urinary AGP by ELISA (Human Orosomucoid ELISA Quantitation Kit; Genway Biotech, Inc., San Diego, Calif., USA).

Using SELDI-MS and cSLE urine, a protein signature was identified for LN consisting of 8 renal biomarkers proteins with mass spectrometry peaks at m/z of (all kDa) 2.7, 22, 23, 44, 56, 79, 100 and 133. These proteins have now been positively identified, as shown in Table 1. Massive albumin excretion was expected, and immunoglobulin chains are likely an epiphenomenon.

Ceruloplasmin (Cp), a glycoprotein and acute phase reactant, is coded on 3q23 and involved in copper metabolism. Cp has a critical physiological role for determining the rate of iron efflux from cells with mobilizable iron and has been proposed as a renal biomarker for SLE in the past. In our studies, urinary Cp correlated with LN severity ($p<0.05$) and is only related to renal but not extra-renal disease activity, as shown in Table 3.

Alpha-1-acid glycoprotein (AGP1) is coded on chromosome 9q34 and is a known predictive renal biomarker in diabetes. We found that AGP1 was strongly correlated with PNGAL, urinary Cp, Tf, and renal disease activity (all $r>0.5$; $p<0.001$), as shown in Table 4.

Lipocalin-like prostaglandin D synthetase (L-PGDS) is involved in nitric oxide regulation. Like AGP1, coded on chromosome 9q34, LPGDS has been implied in essential hypertension development. L-PGDS in urine and serum are sensitive indicators of diabetic renal damage and hypertension.

SELDI-MS peak intensities for L-PGDS, AGP1, Transferrin and Ceruloplasmin are shown in Table 5.

It cannot be excluded that additional renal biomarkers may be covered by the massive albuminuria present in most subjects, an issue that can be addressed by the proposed MALDI-MS (matrix assisted laser desorption/ionization mass spectrometry). Using commercial or well-validated assays in our laboratory, we exactly quantified the amounts of transferrin (Tf), ceruloplasmin (Cp) & alpha-1-acid glycoprotein (AGP1) in plasma and urine, while for lipocalin-like prostaglandin D synthetase (L-PGDS) only SELDI-MS peak intensities are available thus far:

Transferrin (Tf), coded on chromosome 3q22 is, in part, regulated by interferon-α. Tf is involved in iron ion delivery and associated with the innate immune system. Plasma Tf levels have been correlated with SLE disease activity in the past. We found both urinary and plasma Tf significantly increased with renal disease activity (Table 2) and the findings of renal biopsies ($F=3.4$; $p<0.027$).

TABLE 1

| Mass (kDa) and Identity of Urinary Biomarkers | | | | | | | |
|---|---|---|---|---|---|---|---|
| Mass (kDa) | | | | | | | |
| 2.7 | 22 | 23 | 44 | 56 | 79 | 100 | 133 |
| Albumin | Albumin | Immunoglobulin light chain, Lipocalin-like Prostaglandin D synthetase | Albumin | Immunoglobulin heavy chain, alpha1-acid glycoprotein | Transferrin | Albumin | Ceruloplasmin |

TABLE 2

Relationship of transferrin in blood & urine with renal disease activity.

| Median/interquartile range | N:n | Renal SLEDAI score = 0 (N) | Renal SLEDAI score > 0 (n) | p-value† |
|---|---|---|---|---|
| Plasma transferrin (in mg/dl) | 61:25 | 284 (56) | 252 (101) | <0.03 |
| Urine transferrin (in mg/dl) | 61:25 | 0.00 (0.47) | 3 (13.0) | <0.0006 |

†Wilcoxon-Rank Sum test

TABLE 3

Relationship of Ceruloplasmin in blood & urine with renal disease activity.

| Median/interquartile range | N:n | Renal SLEDAI score = 0 (N) | Renal SLEDAI score > 0 (n) | p-value† |
|---|---|---|---|---|
| Plasma ceruloplasmin (in mg/dl) | 61:25 | 33.1 (7.9) | 30.9 (8.5) | 0.48 |
| Urinary ceruloplasmin (in ng/ml) | 28:7 | 696 (1,286) | 15,407 (15,238.4) | <0.003 |

†Wilcoxon-Rank Sum test

TABLE 4

Relationship of AGP1 in blood &urine with renal disease activity.

| Median/interquartile range | N:n | Renal SLEDAI score = 0 (N) | Renal SLEDAI score > 0 (n) | p-value† |
|---|---|---|---|---|
| Plasma AGP1 (in mg/dl) | 7:27 | 92.3 (41.8) | 82.1/43.1 | 0.24 |
| Urinary AGP1 (in ng/ml) | 7:27 | 2,007 (3,463) | 28,898/32,696 | <0.0013 |

†Wilcoxon-Rank Sum test

TABLE 5

Peak Biomarker Intensities by WHO Class of LN determined by kidney biopsy[1]

| Biomarker | Lipocalin-like Prostaglandin D synthetase | Alpha1-acid glycoprotein | Transferrin | Ceruloplasmin |
|---|---|---|---|---|
| All SLE | 0.20 (0.68) | 0.06 (0.82) | 0.05 (0.73) | 0.04 (1.39) |
| No nephritis (n = 11)[2] | 0.04 (0.08) | 0.02 (0.02) | 0.01 (0.00) | 0.01 (0.00) |
| Class 3 or 4 (n = 10) | 0.59 (0.91) | 0.55 (0.50) | 0.62 (0.67) | 1.27 (1.74) |
| Class 5 (n = 11) | 0.84 (1.02) | 1.08 (1.89) | 0.80 (1.05) | 1.51 (1.22) |
| p-Value[3] | 0.0003 | <0.0001 | <0.0001 | <0.0001 |

[1]Values are median (interquartile range) of the intensity peaks on SELDI-MS
[2]Wilcoxon Rank-Sum Test; All p < 0.004 between WHO Class 1 vs. Class 3&4; all p < 0.0022 between WHO Class 1 vs. Class 5
[3]Kruskal Wallis Test for overall differences across groups of SLE patients with different renal pathology

TABLE 6

Demographics and disease outcomes of subjects with cSLE.

| | Parameter | n | % of total | Mean [SE] † |
|---|---|---|---|---|
| Gender (female:male) | 72:13 | 85 | 85%:15% | |
| Race | American-Indian | 3 | 4% | |
| | Asian | 11 | 13% | |
| | African-American | 27 | 32% | |
| | Pacific Islander | 1 | 1% | |
| | Caucasian | 42 | 49% | |
| | Other | 1 | 1% | |
| Ethnicity | Hispanic | 9 | 11% | |
| | Non-Hispanic | 76 | 89% | |
| Age (in years) | | | | 15.5 [0.52] |
| Disease duration (in years) | | | | 5.8 [1.76] |
| Current medications | Prednisone | 65 | 76% | 17 mg/day [1.9] |
| | Hydroxychloroquine | 70 | 82% | |
| | Azathioprine, mycophenolate mofetil | 47 | 55% | |
| | Cyclophosphamide* | 21 | 25% | |
| | Aspirin, NSAIDs | 19 | 22% | |
| | Angiotensin blocking agents | 29 | 34% | |
| Renal biopsies | None available** | 37 | | |
| | WHO Class II | 1 | | |
| | WHO Class III | 8 | | |
| | WHO Class IV‡ | 23 | | |
| | WHO Class V | 16 | | |
| | Time since renal biopsy (in years) | | | 2 [0.35] |

TABLE 7

Disease measures and laboratory testing results of subjects with cSLE.

| SLE Disease parameter | n | Mean [SE]† | Definition of presence of abnormal value | n (%) of tested patients with abnormal values |
|---|---|---|---|---|
| Laboratory Measures | | | | |
| Erythrocyte sedimentation rate | 68 | 23 [2.5] | Increased level of ESR | 48 (70%) |
| Serum creatinine | 85 | | Increased serum creatinine level of age or weight | 3 (4%) |
| Serum complement C3 or C4 | 85 | | Decreased level of C3 and/or C4 | 46 (54%) |
| Anti-ds-DNA antibodies levels | 57 | | Elevated levels of anti-dsDNA antibodies (Crithidia) | 50 (88%) |
| Protein/creatinine ratio | 85 | 0.93 [0.26] | Urine protein/creatinine > 0.2 | 28 (33%) |
| Hematuria | 85 | | At least 5 RBC/Hpf | 14 (16%) |
| Pyuria | 85 | | At least 5 WBC/Hpf | 13 (15%) |
| Granular or heme-granular casts | 85 | | At least 1 cast/Hpf | 15 (18%) |
| Disease Indices | | | | |
| Global disease activity‡ | 85 | 5.3 [0.55] | SLEDAI score > 0 | |
| Renal disease activity - SLEDAI‡ | 85 | 2.1 [0.42] | Renal domain SLEDAI score > 0 | 26 (31%) |
| Extrarenal disease activity - SLEDAI | 85 | 3.21 [0.32] | Extrarenal domain SLEDAI score > 0 | 65 (76%) |
| Global disease damage (SDI)§ | 85 | 0.56 [0.13] | SDI > 0 | 25 (29%) |
| Extrarenal damage | 85 | 0.05 [0.02] | Extrarenal domain SDI score > 0 | 23 (27%) |
| Renal damage | 85 | 0.05 [0.02] | Renal domain SDI score > 0 | 4 (5%) |
| MD assessment of global disease activity | 85 | 2.34 [0.19] | Visual analog scale > 0; range 0-10 | 13 (15%) |

TABLE 7-continued

Disease measures and laboratory testing results of subjects with cSLE.

| SLE Disease parameter | n | Mean [SE]† | Definition of presence of abnormal value | n (%) of tested patients with abnormal values |
|---|---|---|---|---|
| MD assessment of renal disease activity | 85 | 5.44 [0.51] | Visual analog scale > 0; range 0-10 | 19 (22%) |

TABLE 8

Changes of complement levels and urine protein creatinine ratio over time†.

| | | (%, SE) Change of Complement‡ | | Absolute change (SE) in protein:creatinine |
|---|---|---|---|---|
| | Type of Change | C3 | C4 | ratio |
| MD-rated change in global disease activity | Worse | +7% (2%) | +15% (9%) | −0.06 (0.04) |
| | Better or Same | +6% (10%) | +26% (9%) | −0.23 (0.06) |
| MD-rated change in renal disease activity | Worse | −4% (7%) | −15% (10%) | +1.6 (0.15)$ |
| | Better or Same | +28% (3%) | +48% (4%) | −0.61 (0.05)$ |
| Total SLEDAI score between visits | Worse | 0% (1%) | +30% (5%) | +0.1 (0.22) |
| | Better or Same | +45% (6%) | +56% (6%)$ | −0.25 (0.08) |
| Renal SLEDAI scores between visits | Worse | +7% (4%) | −10% (15%) | +0.1 (0.12) |
| | Better or Same | +13% (1%) | +34% (2%) | −0.55 (0.05)$ |

Legend Table 8:
†SE standard error
$p < 0.05 in mixed models correcting for race and gender
‡Complements were not measured by a central laboratory. Thus different ranges of normal were present, making % changes the more relevant group comparator Neutrophil Gelatinase Associated Lipocalin (NGAL, Also Known as: Lipocalin-2).

NGAL is known to be a urinary and plasma/serum biomarker of renal disease activity, damage and findings on renal biopsy. Urinary NGAL (UNGAL) is also expressed by the kidney tubule and interstitium where levels rapidly increase (typically within 24 hours, including 1 to 12 hours) after renal ischemia or nephrotoxin exposure. UNGAL increases much earlier than the traditional urinary or serum markers that typically define acute renal failure. Thus, although elevations in NGAL are not specific to disease activity in SLE, this does not detract from a potentially valuable role for UNGAL in SLE, including for an initial diagnosis of LN, and importantly for detecting the onset of and monitoring worsening renal disease activity and worsening active LN, and for determining and evaluating a response to a therapeutic treatment for LN.

With respect to SLE, both plasma NGAL (PNGAL) and UNGAL are significantly increased in mammalian subjects with childhood SLE compared to juvenile idiopathic arthritis (JIA) or healthy controls, and were unrelated to the subject's age, weight or height. UNGAL can also differentiate between WHO (World Health Organization) class 4 LN vs. Class 5 LN.

NGAL elevations have been noted with several other renal diseases and are not specific for cSLE. Without being bound by any particular theory, it is speculated that UNGAL in cSLE is produced principally by or in response to the injured proximal tubule cells, in direct proportion to the degree and severity of disease. Other cell types such as neutrophils or inflamed vasculature are also possibly a source of UNGAL in cSLE. However, the fact that UNGAL excretion levels correlated with the markers of absolute renal disease activity as well as changes in renal disease activity much stronger than with global disease activity or its changes in global disease activity, suggests that the renal epithelial cells are the major source of NGAL detected in urine. In addition, NGAL produced elsewhere in the body is thought to be almost completely reabsorbed by the kidneys, unless there is concomitant renal injury. This is supported by the observation that PNGAL and UNGAL levels correlate only weakly in cSLE with each other; additionally, healthy controls and children diagnosed with JIA who, despite requiring anti-inflammatory and potentially nephrotoxic medications for disease control, have very low UNGAL levels, generally between 0 and 10 ng/ml urine.

NGAL levels do not differ with subject age, gender and race. The trend towards higher NGAL levels among African-Americans may be due to the higher frequency of renal involvement compared to the participating Caucasian subjects with cSLE (28/37=75% vs. 22/42=52%; p=NS). UNGAL markedly increases with worsening of active LN activity in cSLE subjects.

Renal biopsies were often not obtained in close timely relationship to the study, limiting their suitability to serve as an external standard for NGAL validation. This is because renal histology can change rapidly with therapy, and current laboratory markers are not suitable to accurately estimate the degree of lupus nephritis. In light of the preceding, the present invention has found that UNGAL is a high quality biomarker for SLE renal disease. Although these data have been obtained in young subjects with cSLE, urinary NGAL measurements are also useful for all human patients with SLE, given the similarities in the underlying disease processes of both cSLE and SLE in adults.

The invention provides a means for a clinician to diagnose active LN, or estimate the degree of worsening renal disease activity at an initial assessment, and to monitor the change in renal status over time (e.g. worsening, improving, or remaining the same). The determination of active LN is typically based on the detected level of biomarkers of active LN (i.e. Urinary NGAL, Tf, Cp, AGP1, and L-PGDS, which make up the basic LN-Panel of the invention) in the urine using known methods for obtaining information on protein identity, protein-protein interaction, the level of protein expression, or protein expression profiling.

Using the methods and techniques described herein, quantitative levels of the biomarkers of active LN present in the body fluid can be analyzed with a quantity of urine, blood, plasma and serum to be sampled of typically as little as 10 microliters (µl), up to about 1-5 ml.

Once an indication of active LN has been detected in a cSLE patient, and specific intervention and treatment measures have commenced, the clinician can employ the method of the invention to monitor the progress of any treatment or intervention. Since renal flare can occur at any time in cSLE patients, the clinician can obtain a pretreatment sample of urine, blood serum, or other isolatable body fluid from the subject to determine a baseline biomarker value for that individual. Typically, one or more subsequent post-treatment samples will be taken and analyzed for the continued presence of biomarkers of active LN as the treatment commences and continues. If a baseline value was obtained, these post-treatment values can be compared to the baseline value to determine the relative renal condition of the patient. The treatment can be continued until the presence of the biomarkers in subsequent post-treatment samples either return to baseline values or are no longer detected. As the treatment and intervention ameliorate the flare up, the expression of the renal biomarkers in the subject samples will be correspondingly reduced. The degree of amelioration will be expressed by correspondingly reduced levels of NGAL, Tf, Cp, AGP1, and/or L-PGDS detected in a sample. As healing continues, the method can be used to detect the return to baseline levels or the complete absence of the biomarkers of active LN, signaling the completion of the course of treatment.

Since the biomarkers disclosed herein can be easily detected in subjects within hours of worsening renal disease activity, the present invention, using assays for rapidly detecting and characterizing proteins present at very low levels in a body fluid sample, is suitable for use as an early-onset diagnostic. Biomarker testing of urine, blood, plasma, serum or other body fluid samples from a subject can begin anytime after a suspected change in renal status including LN, including a week, within 24 hours, within 12 hours, within 8 hours, within 6 hours, with 4 hours within 3 hours, within 2 hours, within 1 hour, or within 30 minutes. The subject biomarkers of worsening renal disease activity usually begin to appear at low levels in the body fluid and continue to rise thereafter. The collecting of samples of the body fluid and biomarker assaying can be commenced at intervals throughout the course of treatment to monitor real time changes in renal health status.

If the sample taken is a blood sample, then a serum or plasma sample can be isolated from the blood sample by well known means. If the sample is a urine sample, it can be assayed neat, diluted or unprocessed, or as a derivative processed (for example, centrifuged or concentrated) by well known means.

Following the performing of an assay on the body fluid and obtaining an assay result for the biomarker of choice, the clinician or other trained individual can contrast and compare the body fluid assay with a predetermined biomarker value, expressed in equivalent terms to the biomarker assay, to distinguish the status of the subject from some other benchmarks. For example, in one embodiment, the assay result can be compared to a first predetermined biomarker value that is predictive of the extent of worsening renal disease activity. In another embodiment, the assay result can be compared with a predetermined value that distinguishes a subject that has worsening renal disease activity from a subject that does not have worsening renal disease activity. In yet another embodiment, the assay result can be compared with a predetermined value that predicts subsequent progression to renal failure, wherein an assay result that is at or greater than the predetermined value is indicative of worsening renal disease activity that has or will subsequently develop to renal failure. In still another embodiment, the assay result can be compared with a predetermined value that predicts that the worsening renal disease activity will not subsequently develop to renal failure, and wherein an assay result that is less than said predetermined value is indicative of worsening renal disease activity that has not and will not develop to renal failure. In another embodiment, the assay result can be compared to the level of the biomarker in the respective body fluid of a healthy subject who is not experiencing diminished renal function. The selecting of the predetermined value of the respective renal biomarkers is typically obtained by statistical analysis of a plurality of biomarker assay results, compared against the present condition and progressive condition of the subject, as clinically determined by other standard renal function biomarkers.

The methods of the present invention further include managing subject treatment based on the status of the subject. The invention also provides for such methods where the biomarkers (or specific combination of biomarkers) are measured again after subject management. In these cases, the methods are used to monitor the renal status of the patient, e.g., the response to treatment. Because of the ease of use of the methods and the lack of invasiveness of the methods, the methods can be repeated after each treatment the patient receives. This allows the clinician to follow the effectiveness of the course of treatment. If the results show that the treatment is not effective, the course of treatment can be altered accordingly. This enables the clinician to be flexible in the treatment options.

The method of the present invention for detecting levels of NGAL, Tf, Cp, AGP1, and/or L-PGDS can be made by adapting the methods and kits known in the art for the rapid detection of other proteins and ligands in a biological sample. A rapid one-step method of detecting the biomarker(s) can reduce the time for detecting changes in renal disease activity. A typical method can comprise the steps of: obtaining a sample suspected of containing one of the renal biomarkers disclosed herein; mixing a portion of the sample with detecting antibodies for specifically binding to each of the biomarkers, so as to initiate the binding of the detecting antibodies to the biomarkers in the sample; contacting the mixture of sample and detecting antibodies with immobilized capture antibodies which specifically bind to the biomarkers, which capture antibodies do not cross-react with the detecting antibodies, so as to bind the detecting antibodies to the biomarkers, and the biomarkers to the capture antibodies, to form a detectable complex; removing unbound detecting antibodies, capture antibodies and any unbound sample from the mixture; and then detecting the complex. The detectable antibodies can be labeled with a detectable marker, such as a radioactive label, enzyme, biological dye, magnetic bead, or biotin, as is well known in the art. The detectable antibodies can be attached to a supporting material, such as a membrane, plastic strip, plastic laboratory plate such as those used for ELISA or other high-throughput assays, or any other supporting material, such as those used in other diagnostic kits well known in the art.

EXAMPLES

Example 1: LN Panel Proteins

Children diagnosed with SLE (4) prior to the age of 16 years (n=98) were studied every 3 months for up to 18 months. At each study visit, blood and random spot urine samples for research were obtained, and information on the following laboratory measures was collected: BUN (urea), serum creatinine, serum complement levels C3 and C4, presence of anti-dsDNA antibodies, urine protein:creatinine ratio (normal <0.2), and creatinine clearance approximated according to the Schwartz formula. At the participating centers, kidney biopsies are obtained in SLE patients when abnormal urinalyses cannot be explained by mechanisms other than SLE. Thus all children without kidney biopsies were considered to have SLE without LN. The study was approved by the Institutional Review Board (IRB) of the Cincinnati Children's Hospital Medical Center, and the IRBs of all other participating centers, with informed consent obtained prior to any study-related procedures.

At each study visit, two widely accepted measures of disease activity were completed: the 2 k-version of the Systemic Lupus Erythematosus Disease Activity Index (SLEDAI), and the British Isles Lupus Activity Group (BILAG) Index (6), an index that has been developed specially to assess organ-specific disease activity. SLEDAI or BILAG scores of 0 indicate inactive disease, and higher scores represent higher disease activity. Renal disease activity corresponds to SLEDAI or BILAG renal scores of >0 or >1, respectively. At study entry, the Systemic Lupus International Collaborating Clinics/ACR Damage Index (SDI; 0=no damage) was completed.

Briefly, biomarkers of acute LN were detected on at least two different ProteinChips, and displayed a >100-fold increase in peak intensity between groups. Subsequently, three urine samples from each WHO-class of patients with LN and controls were lyophilized and re-dissolved with Laemmli sample buffer (Bio-Rad Laboratories, Hercules, Calif., USA) for SDS-PAGE, using 8% or 12% Tris-Glycine gels with molecular weight standard markers (Invitrogen, Carlsbad, Calif., USA). Bands that showed the same molecular weights as the candidate biomarker proteins (SELDI-TOF MS) were excised, then digested with trypsin, and recovered for mass spectrometry. One third of the individual band was treated with elution solution [50% formic acid, 25% acetonitrile, 15% isopropanol, 10% water] to extract the proteins contained in each band. These proteins were then analyzed on a normal binding ProteinChip to confirm the aimed mass spectrum. Peptides recovered from the in-gel digest were identified either via peptide mass fingerprints (PMFs) on the SELDITOF platform, or MALDI-TOF/TOF MS via MS/MS fragmentation with sequencing individual peptides. The use of both methods was necessary as albumin or albumin fractions often were present, and none of the various albumin removal approaches [albumin depletion kit (QIAGEN, Qproteome albumin/IgG depletion kit, Valencia, Calif., USA), immunoprecipitation (Dynabeads Protein G, Invitrogen, Carlsbad, Calif., USA), urea treatment, and anion exchange spin column (ProteinChip Q spin column, Bio-Rad laboratories Inc., Hercules, Calif., USA)] succeeded in removing the albumin fraction effectively.

For protein identification by SELDI-TOF MS, samples were allowed to dry on a surface chip target plate followed by matrix application. In this format, the SELDI system may be considered comparable to a conventional MALDI-TOF instrument and can be used to collect PMFs spectra directly. Alternatively, samples were applied onto the ProteinChip SEND-ID Array. The peptide mapping data were standardized using the Allin-One-Peptide Software (Bio-Rad Laboratories Hercules, Calif., USA). For MALDI-TOF/TOF MS, the excised peptides were desalted and concentrated on C18-micro-ZipTips as recommended by the vendor (Millipore, Billerica Mass.) and then spotted on the target plate in 2.5 mg/mL CHCA containing 10 mM monobasic ammonium phosphate dissolved in 50% acetonitrile. The monobasic ammonium phosphate suppresses ionization of matrix clusters and enhances low mass range detection of peptides (10). PMFs and MS/MS fragmentation data were collected for each sample. Both MALDI-TOF and TOF/TOF approaches were used, since the extreme abundance of albumin fragments interfered with the PMF identification for many of the bands.

The acquired peptide data from SELDI-TOF MS were searched via Mascot (Matrix Science, Boston, Mass., USA) database search engine and the International Protein Index (IPI) human protein database. For the MALDI-TOF MS/MS spectra, data were processed using an integrated GPSExplorer interface from Applied Biosystems coupled to a local Mascot Server (Matrix Science) with database searches against the entire NCBInr database. In either case, standard Mascot statistical criteria were used to indicate positive protein identification.

We measured plasma and urinary transferrin (Tf), plasma ceruloplasmin (Cp), plasma $\alpha$-1-acid-glycoprotein (AGP, also: orosomucoid), as well as plasma and urine lipocalin-type rostaglandin-D synthetase (L-PGDS) by immunonephelometry (Dade Behring BNII Prospect, Marburg, Germany). Urinary Cp was quantified by ELISA (Human Ceruloplasmin ELISA Quantitation Kit; Genway Biotech, Inc., San Diego, Calif., USA); and urinary AGP by ELISA (Human Orosomucoid ELISA Quantitation Kit; Genway Biotech, Inc., San Diego, Calif., USA).

The urinary biomarkers of active LN initially consisted of eight proteins with MS peaks-to-charge ratios (m/z) of 2.763, 22, 23, 44, 56, 79, 100, and 133 kDa (3). We identified the 23 kDa band as L-PGDS; the 56 kDa as AGP or orosomucoid; the 79 kDa as Tf; and the 133 kDa as Cp, respectively. The remaining four bands represented albumin or albumin fragments which were not further examine for their relationship to the features of LN because we were unable to extract any specific proteins that might have been contained in these bands by our methods. In the following, the plasma concentrations of Tf, Cp, AGP and L-PGDS are reported in mg/dL; urinary concentrations of the Biomarkers of active LN are reported as: 1) absolute concentrations in the urine: Tf and L-PGDS in mg/dL, Cp and AGP in ng/mL urine, respectively; 2) corrected for urinary creatinine (in mg/mL); and 3) corrected for nonselective proteinuria as estimated by the protein:creatinine ratio.

Figure 2:
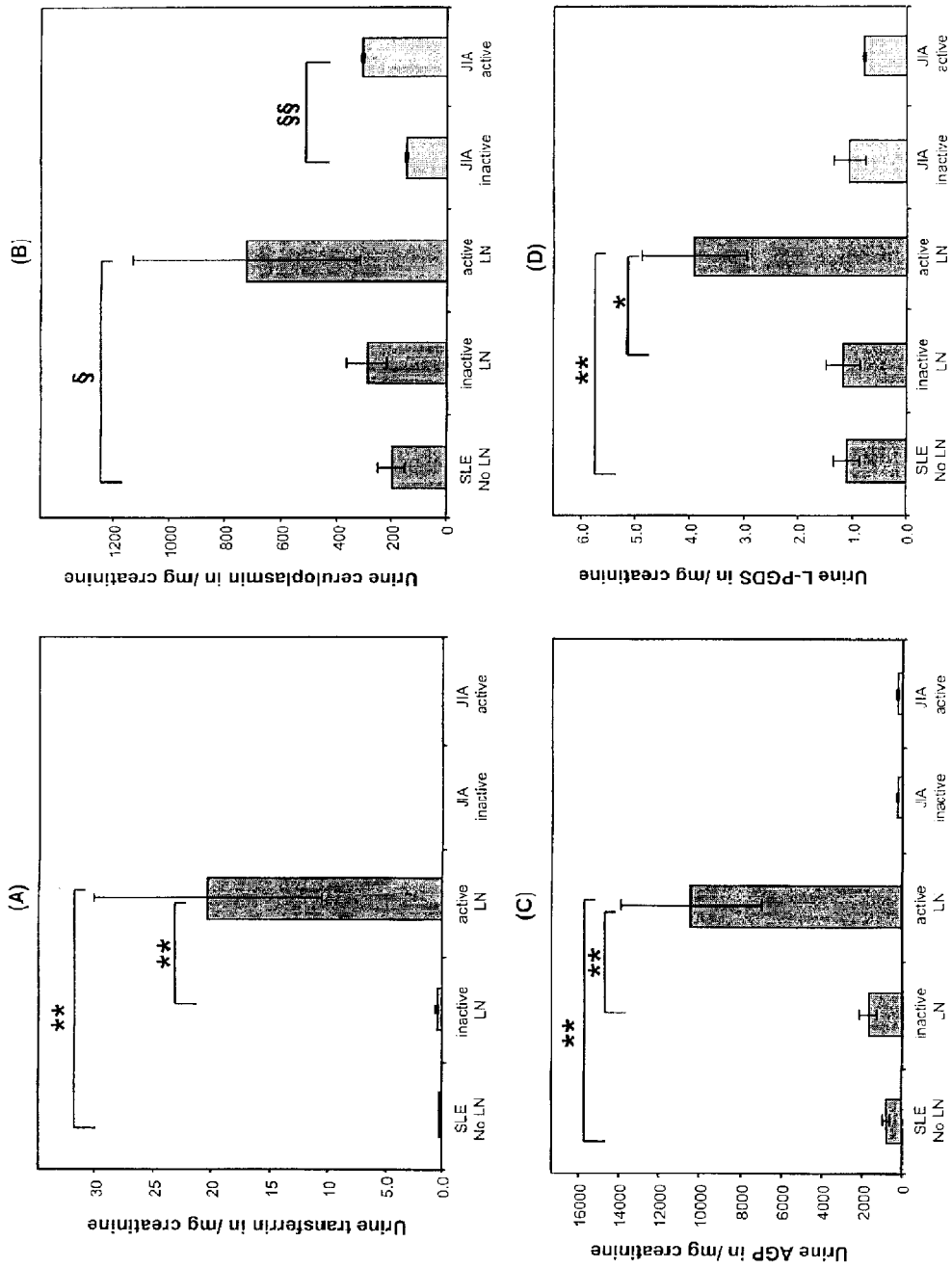
FIG. 2 is a graph showing urinary concentration of LN panel protein excretion standardized by urine creatinine (mg/mL urine). Significant differences between groups are indicated as follows: *=P<0.0005; **=P<0.0001; §=P<0.05; §§=P<0.001.

LN Panel Proteins in SLE Patients:

Proteins in the LN panel were unrelated to SLE patients' weight, gender, race, ethnicity (Hispanic/Non-Hispanic), the use of angiotensin blocking medications, or disease duration. FIGS. 1 and 2 depict the comparison of urinary concentrations of the LN panel proteins considering absolute levels (per dL or mL of urine; FIG. 1), or levels standardized by urinary creatinine (FIG. 2), respectively. SLE patients with active LN had much higher levels of all proteins in the LN panel per mL or dL of urine (FIG. 1) or standardized by urinary creatinine (FIG. 2), with statistically significant differences indicated in the figures. Use of the BILAG instead of the SLEDAI to classify SLE groups according to LN activity yielded comparable results as shown for the SLEDAI in FIGS. 1 and 2.

LN Panel Proteins Differentiate Better than Traditional Measures with the Features of LN:

Table 9 provides a cross-sectional comparison of proteins in the LN panel and traditional laboratory measures for their ability to identify active LN or renal damage. Besides the protein:creatinine ratio, the levels of none of the other traditional laboratory markers, including serum creatinine and BUN (data not shown), demonstrated important differences among patients with active vs. inactive LN. Amongst seven SLE patients with renal damage, both the levels of plasma Tf and all LN panel proteins were significantly higher than in SLE patients without renal damage. However, six patients with renal damage had concomitantly active LN. The $AUC_{ROC}$ was calculated to assess the concurrent validity of the proteins in the LN panel and the traditional renal biomarkers to diagnose the presence of active LN as measured by the SLEDAI and the BILAG, respectively. Individual urinary proteins in the LN panel had an $AUC_{ROC}$ ranging from 0.68 to 0.81, with the $AUC_{ROC}$ for all proteins in the LN panel together at 0.84 (SLEDAI) or 0.85 (BILAG). Conversely, the $AUC_{ROC}$ of the traditional renal biomarkers (creatinine clearance, complements, dsDNA antibodies, BUN) was <0.63. Thus, individual urinary proteins in the LN panel were all better diagnostic markers of active LN than traditional renal biomarkers, performing in the fair to good range according to current ROC interpretation standards. An exception was the urine protein:creatinine ratio with an $AUC_{ROC}$ at 0.91 (SLEDAI) and 0.85 (BILAG), respectively.

Figure 3:
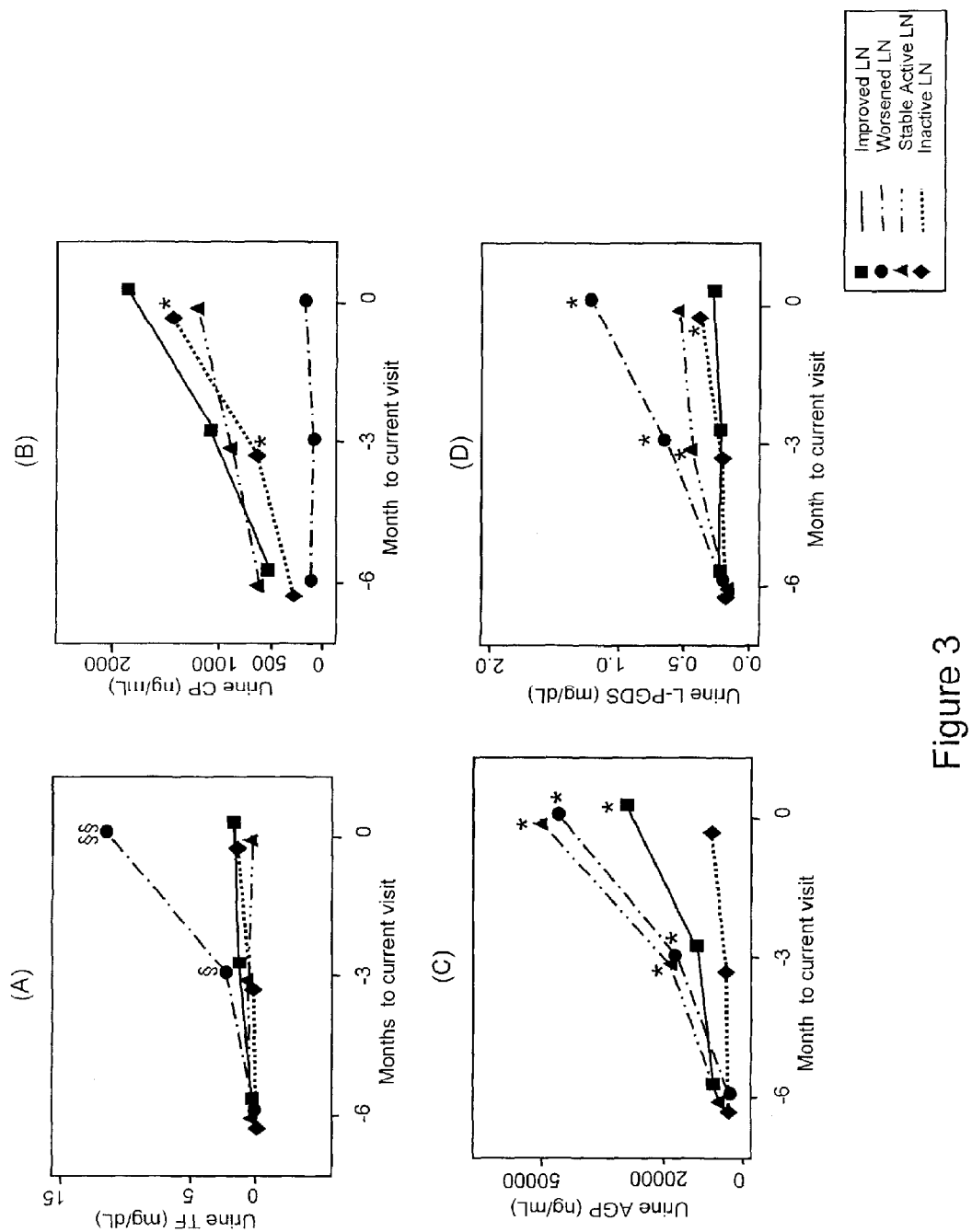
FIG. 3 is a graph showing changes of LN panel proteins in relationship to future changes in LN activity.

Proteins in the LN Panel May Predict the Future Course of LN:

FIG. 3 depicts the absolute levels of urinary proteins in the LN panel over time in relation to changes in LN activity as measured by the SLEDAI. Values are geometric means Panel (A), (B), (C), and (D) show changes of uncorrected urinary levels of Tf, Cp, AGP and L-PGDS at months −6, −3 and 0, respectively. Month 0 is the time point when the clinic diagnosis of the course of LN is made. 'Improved LN' describes the course of LN with decreasing renal SLEDAI scores; 'Worsened LN' describes the course of LN associated with an increase of the renal SLEDAI scores; 'Stable active LN' describes patients with stable renal SLEDAI scores >0; and 'Inactive LN' describes the course of continuously inactive LN (renal SLEDAI=0). Significant differences in the levels between visits are indicated in the plots as follows. §=P<0.009; §§=P<0.0001; *=P<0.001

As shown in FIG. 3, urinary levels of Tf, AGP and LPGDS significantly increased (SLEDAI: all p<0.009) at least 3 months prior to the clinical diagnosis of worsening LN activity and continued to be elevated at the time of the clinically diagnosed LN flare. Cp levels did not show a consistent pattern with the course of LN. None of the traditional biomarkers, including the protein:creatinine ratio, was predictive of the course of LN. Similar results were observed when the BILAG instead of the SLEDAI was used to determine the course of LN.

Data Analysis.

EXCEL XP (Microsoft Inc., Redmond, Wash.) and SAS 9.1 (SAS Institute Inc., Cary, N.C.) were used for analysis. Means and standard errors (SE) values were calculated as measures of central tendency. Groups of subjects were assessed for statistically significant differences using analysis of variance (ANOVA). For cSLE subjects, plasma and urinary NGAL levels, the values of laboratory parameters (serum creatinine, glomerular filtration rate, proteinuria, urinary protein:creatinine ratio, anti-dsDNA antibodies, hemoglobin), and the scores of disease measures (SLEDAI-2K, BILAG, SDI) were correlated using Pearson correlation coefficients (r). Mixed models correcting for differences in gender and race were used to assess changes of NGAL for important differences over time. The Tukey procedure was done for post-hoc testing.

We also inspected the central tendency, dispersion and skewness of the protein levels in the Lupus Nephritis Panel and found them to all fit well into normal distributions after log transformation. Hence, log transformed protein levels in the Lupus Nephritis Panel were used in the formal statistical analyses, and results related to the biomarkers of active LN are presented using geometric means after their log transformed means were converted back to original values by taking exponentials. Using data from the first study visit only, Lupus Nephritis Panel concentrations in three groups of SLE patients (children with active LN; those with inactive LN and those without LN) and among two control groups with active JIA or inactive JIA, respectively, were tested for statistically important differences under a multivariate fixed effect model (or ANOVA model) framework, after adjusting for patients' characteristics such as age, gender and race. Active LN was defined as a renal SLEDAI score >0 or a renal BILAG score >1, respectively. For analysis of longitudinal data with repeated observations on each patient, a random effect (i.e. the patient) was added to the previous fixed effect models to account for within-patient correlation. Receiver operating characteristic (ROC) curves were constructed, and the area under each ROC curve ($AUC_{ROC}$: range 0-1) was calculated to assess performance of the Biomarkers of active LN in discriminating between the presence versus absence of LN activity. An $AUC_{ROC}$ of 1.0 represents a perfect biomarker whereas a value of 0.5 is no better than expected by chance. Statistical computations were conducted using SAS version 9.1 (SAS, Cary, N.C., USA) software. P-values <0.05 were considered statistically significant.

There is a need for high-quality accurate biomarkers to judge LN activity and renal damage with SLE. In this study, we chose a proteomic approach for the discovery of novel LN biomarkers and identified a set of Proteins in the LN panel (i.e. Tf, Cp, AGP and LPGDS). In quantitative analysis, particularly urinary rather than plasma levels of the LN panel proteins increased significantly with the presence of active LN. Different from all traditional laboratory measures of LN, we have initial evidence that Tf, AGP and L-PGDS constitute predictive biomarkers of active LN.

We found high and increasing urinary levels of Tf associated with active LN and impending worsening of LN flares. Tf is co-regulated with interferon-α, involved in iron delivery, and the innate immune system. Plasma Tf levels were correlated to global SLE disease activity in the past. Thus our study confirms these earlier findings in SLE, and new evidence is provided that urinary Tf excretion may represent a predictive biomarker for LN. Cp plays a critical physiological role in controlling the rate of iron efflux from cells with mobilizable iron. Like Tf, plasma Cp has been recommended as a marker of global SLE disease activity. Conversely, our results support that urinary Cp concentrations only differ with LN activity rather than extrarenal disease activity.

AGP is a predictive biomarker for diabetic renal disease, and we provide initial evidence that this is also the case for LN. More importantly, urine concentrations of AGP (similar to Tf and L-PGDS) appear useful to anticipate LN flares, i.e. these markers may allow clinicians to preemptively adjust therapy prior to the appearance of overt worsening of LN. Previous studies proposed plasma AGP to be a biomarker of SLE global disease activity. Our results support this (data not shown) but we also provide evidence that urinary AGP constitutes a biomarker of LN rather than extrarenal disease activity. Lipocalins play a role in many biological processes, among them immune responses and prostaglandin synthesis. L-PGDS, a lipocalin, is involved in nitric oxide regulation and the induction of apoptosis in the kidney. L-PGDS has not been previously found to be a LN biomarker. Urine and plasma L-PGDS are considered sensitive indicators of chemotherapy-induced renal damage and diabetes-associated hypertension. We found urinary L-PGDS unrelated to the creatinine clearance in both JIA and SLE; L-PGDS also did not significantly change with cyclophosphamide exposure in SLE patients. Reason for these discrepancies might be that our patients had all normal or only minimally decreased creatinine clearance, and that there was at least a 3-week time-lag from a previous intravenous cyclophosphamide dose.

At present, there is no universally accepted gold standard for the measurement of LN activity. For this study, we chose to use the two widely accepted SLE disease activity indices (SLEDAI, BILAG). The relevance of our findings is strengthened by the fact that the LN panel proteins performed similarly well to capture and anticipate the course of LN, irrespective of the index used. Compared to the BILAG, the SLEDAI considers only proteinuria and the urinary sediment in the calculation of the LN activity score. Thus, a close association between the protein:creatinine ratio and LN activity and an $AUC_{ROC}$ were expected when using the SLEDAI. Given the sensitivity of moderately elevated protein:creatinine ratio to angiotensin blocking medications and its unproven ability for predicting LN flares, we consider Tf, CP, AGP and L-PGDS to be promising LN biomarkers, as their levels do not seem to change with the use of angiotensin inhibiting medications and even help discriminate patients who are at risk of a future LN flare.

In summary, Tf, Cp, AGP and L-PGDS are promising LN biomarkers. Their initial validation suggests superior measurement properties compared to most traditional LN biomarkers and that Tf, AGP and L-PGDS are candidates of a novel set of predictive LN biomarkers. Additional validation studies are mandatory to evaluate the usefulness of such a LN Renal Panel to predict the course of LN, the severity of kidney pathology, and the future development of renal damage with SLE.

In light of the above, the invention provides a means for a clinician to estimate the degree of active lupus nephritis at an initial assessment, and to monitor the change in renal status over time (e.g. worsening, improving, or remaining the same). The determination of a change in renal status is typically based on the detected level of biomarkers of active LN (i.e. Tf, Cp, AGP1, and L-PGDS, and UNGAL, which make up the basic LN-Panel of the invention) in the urine using known methods for obtaining information on protein identity, protein-protein interaction, the level of protein expression, or protein expression profiling.

Using the methods and techniques described herein, both qualitative and quantitative levels of the biomarkers of active LN present in the body fluid can be analyzed and estimated. The clinician can select the qualitative method, the quantitative method, or both, depending upon the status of the patient. For urine samples, the quantity of urine to be collected is typically less than 1 milliliter (ml), and more typically less than 10 microliters (μl). A typical sample can range from about 1 μl to about 1 ml. Typically the larger quantities of a urine sample (about 1 ml) are used for quantitative assays. Typically, these small levels of urine are easily and readily available from cSLE subjects. Typical blood volumes are the same as typical urine volumes, and are also typically easily available from cSLE subjects.

Example 2: Urinary NGAL

Study.

With approval of the institutional review boards of the participating institutions, children fulfilling American College of Rheumatology Classification Criteria for SLE prior to the age of 16 years (cSLE) were studied during routine visits to the pediatric rheumatology clinics. A convenience sample of 30 children diagnosed with juvenile idiopathic arthritis (JIA) was recruited as disease controls. Samples of healthy controls (n=50) were obtained from The Cincinnati Genomic Control Cohort assembled by the Cincinnati Children's Hospital Medical Center. Children diagnosed with cSLE were studied longitudinally every 3 months, while for JIA and healthy controls cross-sectional samples were available only. Random urine samples were collected on all subjects.

NGAL levels in urine were quantified by ELISA using an NGAL ELISA KIT (KIT 036; AntibodyShop, Grusbakken, Denmark) that specifically detects human NGAL. The assay was performed as per manufacturer's protocol. Briefly, 100 μl of NGAL standards or diluted samples (urine) were applied into pre-coated microwells in duplicates. Microwells were then incubated for one hour at room temperature and subsequently washed with washing buffer. In succession, biotinylated NGAL antibody and HRP-streptavidin were incubated in the wells for one hour each with shaking at 200 rpm. TMB substrate was added for 10 minutes in the dark before adding stop solution. Finally, NGAL concentration was measured at 450 nm wavelength in each well with a reference reading at 620 nm in blank wells. The intra-assay coefficient of variation was 2.1 (range: 1.3-4.0) % in urine. Inter-assay variation was 9.1 (range: 6.8-18.1) % in urine. Urine creatinine was measured using quantitative colorimetric Microplate Assay Kit (Oxford Biomedical Research, Oxford, Mich., USA) to standardize urinary NGAL for changes in urine concentration.

Disease Activity and Disease Damage.

For participants with cSLE, global disease activity and relevant changes of global disease activity were measured by the Systemic Lupus Erythematosus Disease Activity Index (SLEDAI-2K; range 0-105). Extrarenal disease activity was defined as the summary score of the SLEDAI-2K excluding the scores accrued in the renal domain of the SLEDAI-2K. Renal disease activity was defined as the sum of the SLEDAI-2K scores accrued in the renal domain of the measure. Higher SLEDAI-2K scores represent more active disease.

Kidney Biopsies.

All participating centers perform kidney biopsies in any cSLE patient who has abnormal urinalyses that cannot be explained by mechanisms other than SLE. Because some renal biopsies were obtained prior to the introduction of the new classification system of SLE nephritis, the original system was used. There was no information on the activity and chronicity scores of the biopsy specimens. Laboratory Testing recorded for the study included serum BUN, creatinine, urinalysis and microscopy; urinary protein:creatinine ratio (normal <0.2), serum complement levels C3, C4 (categorized as normal or low), hemoglobin, ESR, and anti-dsDNA antibodies (categorized as negative or positive/elevated).

Relevant Changes in cSLE Disease Course.

Worsening of overall cSLE disease course between visits was measured in two ways. First, physician-rated worsening of global disease as defined by an increase in the scores of the disease activity estimate on a visual analog scale (MD-VAS; range 0-10); second, by an increase in the scores of the overall domain score of the SLEDAI-2K. Renal disease activity was assessed in a similar fashion. Global or renal disease activity was considered 'unchanged' or 'improved' in cases where the MD-VAS or the SLEDAI-2K suggested that the cSLE subject's disease was stable or even had improved, respectively. Additionally, physicians completed a Likert scale (i.e. a questionnaire wherein respondents specify their level of agreement to a statement) to indicate whether there were renal flares, stable renal disease, or improving renal disease between study visits.

Control Population.

Plasma and urine specimens of the healthy controls generously were donated by The Cincinnati Genomic Control Cohort. Information on the review of systems as well as demographic information was available. For participants with JIA, the results of routine urinalyses and serum creatinine testing ordered to screen for NSAID- and/or methotrexate-related toxicity were recorded. In addition, using the standardized records, information pertaining to subject demographics and the JIA core response variables was obtained, including ESR (erythrocyte sedimentation rate), physician-rated disease activity on a visual analog scale (MD-VAS; range 0-10), the number of joints with active arthritis, and those with limited range of motion.

Data Analysis.

EXCEL XP (Microsoft Inc., Redmond, Wash.) and SAS 9.1 (SAS Institute Inc., Cary, N.C.) were used for analysis. Means and standard errors (SE) values were calculated as measures of central tendency. Groups of subjects were assessed for statistically significant differences using analysis of variance (ANOVA). For cSLE subjects, plasma and urinary NGAL levels, the values of laboratory parameters (serum creatinine, glomerular filtration rate, proteinuria, urinary protein:creatinine ratio, anti-dsDNA antibodies, hemoglobin), and the scores of disease measures (SLEDAI-2K, BILAG, SDI) were correlated using Pearson correlation coefficients (r). Mixed models correcting for differences in gender and race were used to assess changes of NGAL for important differences over time. The Tukey procedure was done for post-hoc testing.

As noted above in the definitions section, Urinary NGAL (UNGAL) excretion is herein presented in two ways; 1) UNGAL-ml—the amount of urinary NGAL in ng/ml of urine ("unadjusted UNGAL"); and 2) UNGAL-crea—the amount of urinary NGAL in ng/mg of urine creatinine, to correct for differences in NGAL due to urine dilution ("adjusted UNGAL").

Results.

Data of 85 subjects with cSLE were available, and 52 of them had at least one follow-up visit (total number of visits: 132). The demographic information of the cSLE subjects participating in the study is summarized in Table 6 and the results of their laboratory testing are shown in Table 7. The mean time+SE between the first study visit and the time of the renal biopsy was 2+0.35 years for those subjects who had biopsies (N=48). At baseline, the mean+SE of UNGAL-ml and UNGAL-crea of the cSLE subjects was 44.6+7.3, and 29.2+4.6, respectively. UNGAL-ml was strongly correlated with UNGAL-crea (r=0.8; p<0.0001).

JIA Controls.

Thirty children with JIA (female:male=27:3; mean age+SE:15.6+0.1 years) participated in the study. There were four African-American and 26 Caucasian subjects with JIA, none were Hispanic. JIA subjects were treated with NSAIDs alone (n=2), methotrexate (MTX) alone (n=8), or the combination of NSAIDs and MTX (n=12); 11 JIA subjects were treated with biologic medications (etanercept, abatacept, infliximab, adalimumab) alone or in combination with NSAIDs and/or MTX. The mean+SE number of active joints and joints with limited range of motion was 2.3+0.3 and 1.7+0.1, respectively; ESR or CRP (C-reactive protein) levels were elevated in 7 (25%) of the 24 JIA controls with available data. None of the JIA controls had a history of chronic or a recent acute urinary tract infection, and all had normal urinalyses and normal serum creatinine levels.

The mean+SE of UNGAL-ml and UNGAL-crea were 24+3.8, and 17.5+3.1, respectively. Furthermore, NGAL (plasma, urine) did not differ with exposure to NSAIDs or biologic medications.

Healthy Controls.

The 50 healthy children (female:male=28:22) had a mean+SE age of 14.8+0.05 years. There were 16 African-American and 34 Caucasian healthy controls, and none were Hispanic. The mean+SE of UNGAL-ml and UNGAL-crea were 15+0.4, and 7.9+0.2, respectively.

Cross-Sectional Differences in NGAL Levels Between cSLE Subjects and Controls.

Using ANOVA and Tukey post-hoc testing, differences in NGAL levels between groups of subjects (cSLE, JIA subjects, and healthy children) were assessed. UNGAL did not differ significantly between JIA and healthy controls. Conversely, cSLE subjects had significantly higher UNGAL-ml and UNGAL-crea than controls. Thus, NGAL in urine is elevated in cSLE compared to JIA or healthy controls.

NGAL and Subject Biometrics, Vitals, and Race.

Irrespective of diagnosis (JIA, cSLE, or healthy), NGAL (urine) did not differ with subject weight, height or age. Only among cSLE subjects, Caucasians had a trend towards lower NGAL (urine). The same was true for males as compared to female cSLE subjects. UNGAL correlated with the blood pressure of JIA and cSLE subjects.

NGAL—Relationship to cSLE Disease Features: Correlation of NGAL with Select cSLE Laboratory Parameters and Treatments.

NGAL (urine) was unrelated to the daily dose of prednisone, creatinine clearance, complement C3 and C4 levels, and ESR. NGAL (urine) levels did not significantly differ with the use of immunosuppressive medications. There was a trend towards higher UNGAL in subjects treated with angiotensin blocking drugs (for UNGAL-crea: 42+8.2 versus (vs.) 24+5.4). UNGAL correlated moderately with the urinary protein:creatinine ratio.

Urinary NGAL and Disease Activity.

UNGAL correlated moderately with active renal disease, as measured by the SLEDAI-2K, where the mean+SE of UNGAL-crea was 45.4+11.6 with active renal disease (renal SLEDAI-2K>0), and only 21.7+3.7 in subjects with inactive renal disease. Further, the mean+SE of UNGAL-crea with active global disease (SLEDAI-2K>0) was 31.7+5.2, which differed from that of inactive global disease (SLEDAI-2K=0) which was 15.6+7.3. UNGAL-crea did not significantly change between active extrarenal disease (extrarenal SLEDAI-2K>0) and inactive extrarenal disease (SLEDAI-2K=0), where the mean UNGAL-crea values were 65.3+5.1 and 54.5+7.3, respectively.

NGAL and Findings on Renal Biopsy.

Renal damage as measured by the damage score and data index (SDI) was present in only four subjects, hence rare in this cohort. UNGAL-crea, but not UNGAL-ml, differed between groups of cSLE subjects with various degrees of renal involvement (based on WHO class) when compared by ANOVA, as shown in Table 8 above.

Relation of NGAL with Worsening cSLE Disease Activity Over Time.

While UNGAL typically remains unchanged in cSLE subjects with stable disease activity, with worsening global disease activity subjects had a mean increase of unadjusted UNGAL (UNGAL-ml; in ng/ml urine) of 11.5+6.4 (a 156% increase). With worsening renal disease activity, cSLE subjects had a mean increase of unadjusted UNGAL of 36.6+12.1 (380%). UNGAL adjusted for urine creatinine (UNGAL-crea; in ng/ml urine creatinine) yielded similar changes as those for unadjusted UNGAL. While PNGAL did increase with worsening of cSLE disease activity, it did not significantly increase, and the increase was to a lesser degree than UNGAL. Changes of UNGAL in relation to worsening disease activity are summarized in FIGS. 4 and 5. UNGAL-ml and UNGAL-crea showed similar relationships to changes in disease activity.

UNGAL and Worsening of cSLE Disease Activity.

Figure 4:
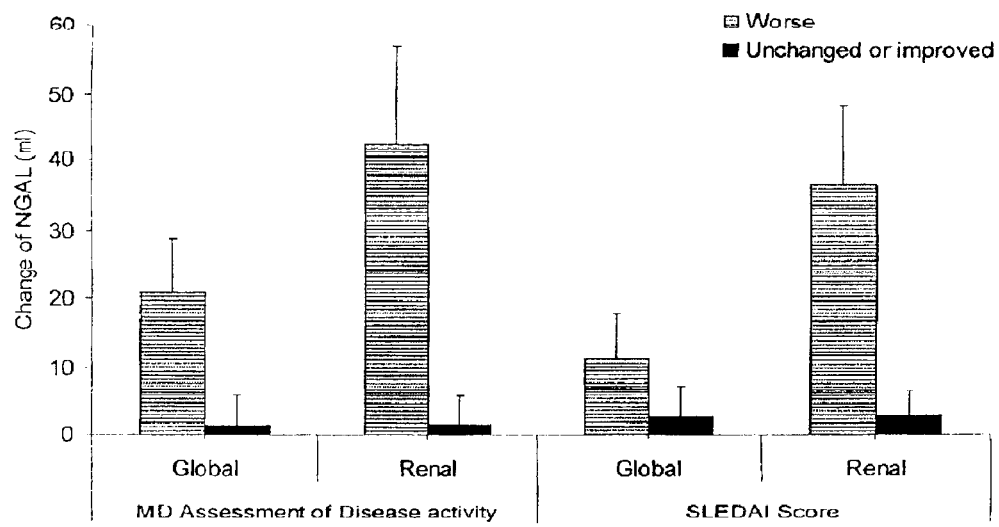
FIG. 4 is a graph showing absolute changes in urinary NGAL (UNGAL) under worsening versus unchanged or improved disease activity.
Figure 5:
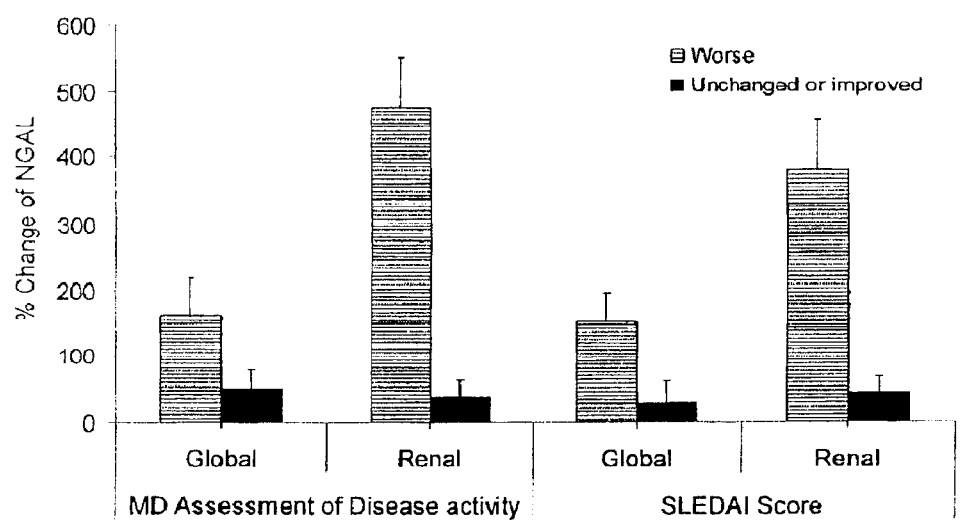
FIG. 5 is a graph showing percentage changes of UNGAL under worsening versus unchanged or improved disease activity.

UNGAL levels often increased significantly with worsening of global disease activity, but were particularly increased with worsening renal disease activity, irrespective of the external standard used (MD-VAS, SLEDAI-2K). Changes of UNGAL are shown in FIGS. 4 and 5. UNGAL-ml and UNGAL-crea showed similar relationships to changes in disease activity. The mean+SE of absolute levels of UNGAL (ng/ml) increased significantly with worsening of renal disease activity ($p<0.01$), irrespective of the external standard (MD-VAS, SLEDAI-2K) chosen (FIG. 4). The same was true when the mean+SE of relative changes (%) were considered (FIG. 5). For example, with worsening renal disease activity (renal SLEDAI-2K>0) the mean+SE of UNGAL-ml and UNGAL-crea rose by 380% and 125%, or 27+12 and 9+8, respectively (all $p<0.01$). Although UNGAL increases with worsening of global or overall disease activity, such changes were less pronounced, and only reached statistical significance when the MD global assessment was used as external standard.

NGAL and Physician-Rated Clinically Significant Changes in Renal Disease.

A Likert scale was completed by the treating physician to indicate whether cSLE subjects' renal disease had improved (n=16), worsened (n=8), or was stable (n=17) between visits. The mean+SE of UNGAL-ml changes were −56.8±6.0 with renal improvement, +26.8±12.3 with renal flare, and +14.9±0.5 when renal disease was considered to be stable. The respective changes of UNGAL-crea were −51.5±6.2, +7±7.7, and +5.6±0.5.

Figure 6:
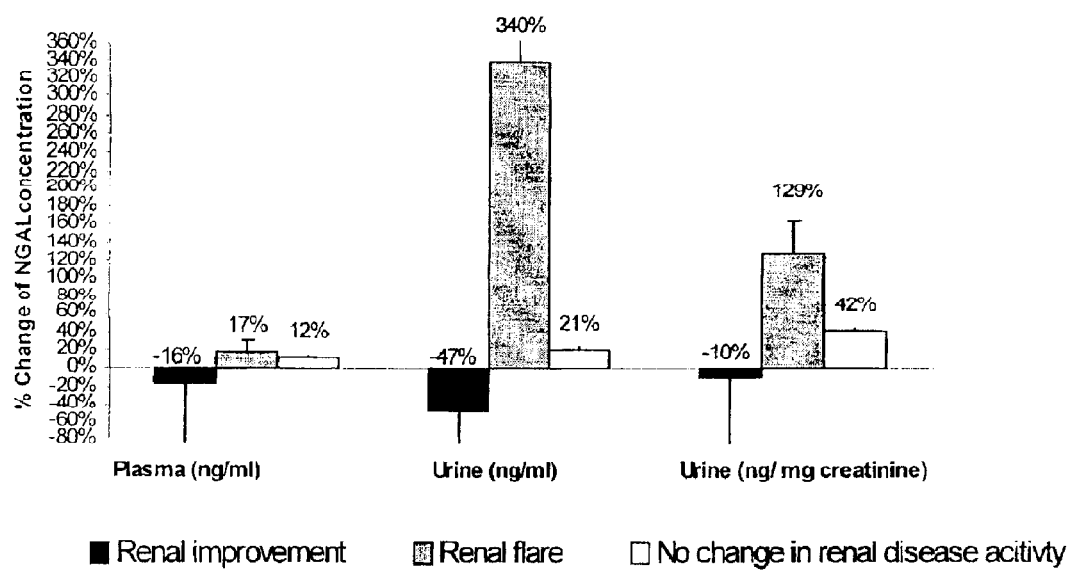
FIG. 6 is a graph showing percentage changes of both PNGAL and UNGAL under comparative conditions of renal improvement, renal flare and no change in renal disease activity.
Figure 7:
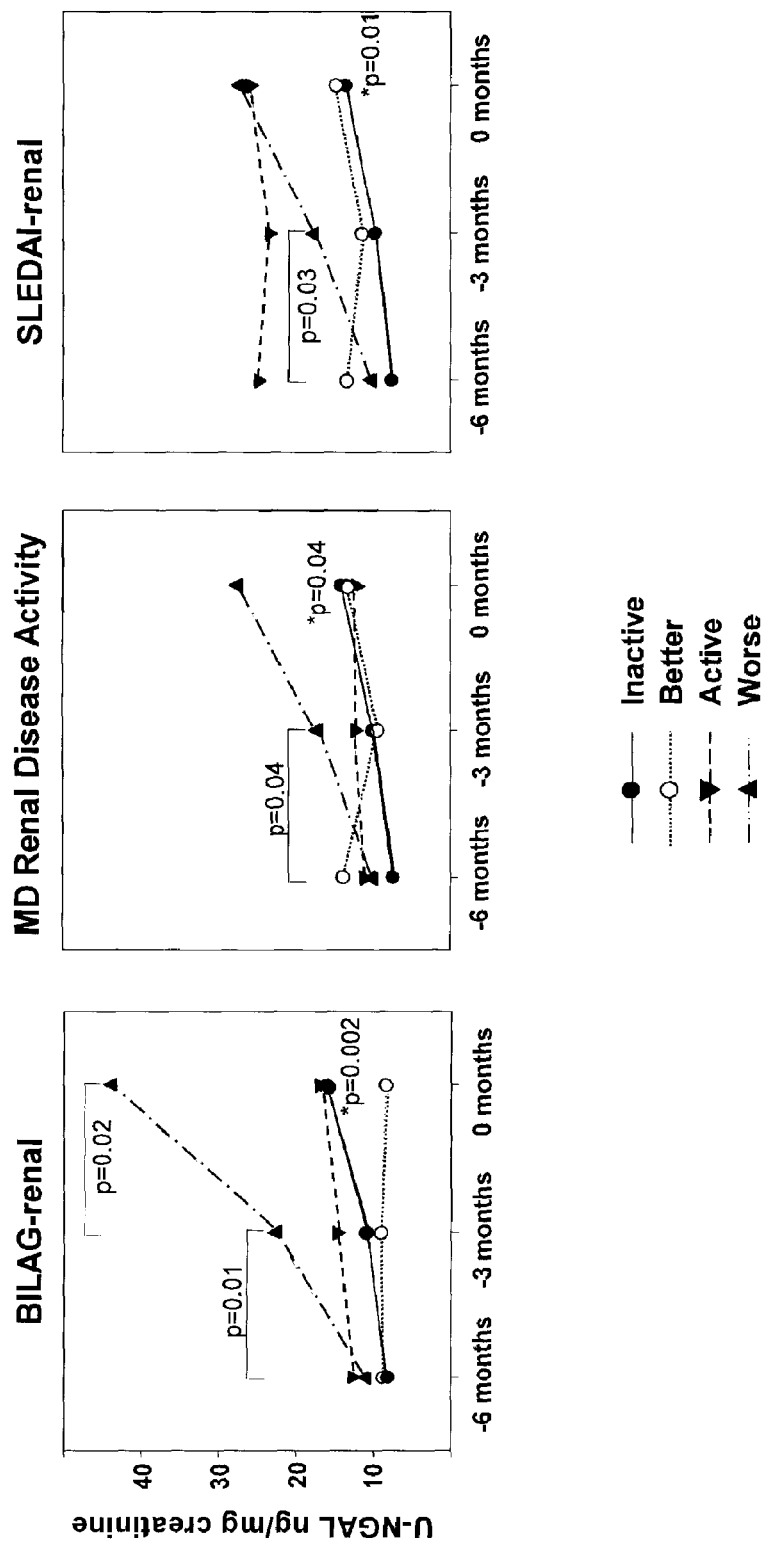
FIG. 7 has three panels showing mean urinary U-NGAL/ urine creatinine ratios according to three renal disease activities: BILAG, MD assessment, and SLEDAI.

FIG. 6 provides a comparison of the relative (%) changes of NGAL in plasma (data not shown elsewhere) and urine with changes in renal disease activity, as PNGAL remained relatively stable despite changes in renal disease. This is different from changes in UNGAL-ml and UNGAL-crea which increased by 340% and 129% with renal flares, while with improving renal disease UNGAL-ml and UNGAL-crea decreases of 47% and 10% were observed, respectively. On average, only small increases of UNGAL occurred in cSLE subjects whose renal disease was considered unchanged. In contrast to changes of PNGAL, differences in UNGAL-ml and UNGAL-crea, but not those of PNGAL, reached statistical significance at $p<0.01$ and $p<0.05$, respectively.

Our cross-sectional and longitudinal data indicates that UNGAL rather than PNGAL is closely related to renal disease activity in cSLE. Irrespective of whether urinary NGAL excretion was standardized for urinary concentration (UNGAL-crea) or not (UNGAL-ml), worsening renal disease activity resulted in marked increases of UNGAL. Plasma concentrations of NGAL fluctuated widely in cSLE, and there was no significant increase with renal disease activity change. Thus UNGAL represents a renal biomarker of lupus nephritis in patients with cSLE, with increased levels present in both subjects with active lupus nephritis or renal damage due to cSLE.

In the current cohort with its relative short disease duration of 5.8 years of subjects with renal biopsy-proven lupus nephritis, disease damage was rare, prohibiting a statistical analysis of the relationship of NGAL and disease damage.

Example 3: Urinary NGAL in Worsening LN 147 children with cSLE were enrolled at nine centers in North America, and assessed for urine and plasma NGAL by ELISA every 3 months (a total of 510 visits). The global and LN disease course was determined in 3 ways: MD assessment of global/renal cSLE, and the extrarenal and renal domain scores by the SLEDAI-2K and BILAG indices. Mixed effect models were used to test for significant differences between groups adjusted for age, race, and sex. The level of NGAL in the urine and plasma/serum was detected at levels by ELISA kits (NGAL ELISA KIT 036; Antibody-Shop, Grusbakken, Denmark) and methods well known and disclosed herein. The change in disease activity compared between the last visit (0 months) and the visit prior (−3 months) was categorized based on: the status of the LN diagnosis as active LN, improved or better LN, inactive LN, and worsening active LN; and urine level NGAL, standardized for urinary creatinine (U-NGAL crea) and plasma level NGAL (P-NGAL); and mixed effects model statistics to analyze variance between groups (SAS) and to account for age, race and sex P-NGAL levels increased by as much as 27% (MD assessment; $p<0.001$) prior to severe global flares and were unchanged or decreased with unchanged or improved global cSLE. P-NGAL levels were increased by 20% and 19%, respectively, prior to worsening of global cSLE as measured by the respective domains of the SLEDAI ($p<0.001$) and BILAG ($p<0.01$). P-NGAL levels rose by 26%, 37% and 9%, respectively, prior to worsening renal disease activity as measured by the MD-renal assessment ($p<0.001$), the BILAG-renal ($p<0.001$) and SLEDAI-renal domain scores (p=0.296). Urine NGAL was unrelated to extrarenal disease activity (BILAG-extrarenal, MD global, SLEDAI-extrarenal).

Standardized by urine creatinine, urine NGAL correlated with present LN activity and was also predictive of future LN flares (see Table 10). The data of 3 visits was used from each patient. Visit 3 denotes most the last or recent (time 0) visit, and visit 1 and 2 occurred 6 months and 3 months prior to visit 3, respectively. For patient with worsening LN activity at visit 1 (time 0), urine NGAL levels increased between visit 2 (−3 months) and visit 3 (−6 months) by 103.9%, 71.2% and 69.7%, between visit 1 (time 0) and visit 2 (−3 months), as measured at the time of visit 1 (time 0) by BILAG-renal score (p: 0.01), MD assessment (p: 0.04), and SLEDAI-renal score (p: 0.03), respectively. On the contrary, in the group with improved or unchanged LN activity between visit 2 and 3, urine NGAL remained constant or decreased between visit 1 and 2 (P>0.05). Urinary NGAL levels were of course detected in units of ng NGAL/ml of urine, and then normalized for the level of creatinine in the urine. Thought eh NGAL levels are shown in ng NGAL/mg urinary creatinine, it is understood by persons skilled in the art that the respective percentage increases between visits would be comparable for NGAL levels expressed in ng NGAL/ml urine.

The urinary NGAL levels, in ng NGAL/mg creatinine, at visits 1, 2 and 3 for each renal assessment, are shown in FIG. 9.

P-NGAL has predictive validity for renal and extra-renal disease activity.

Urine NGAL changes are specific to the course of LN and have concurrent and predictive validity for the course of LN. Because urine NGAL increases prior to the occurrence of renal flares it may be useful for medical decision making to help abort impending renal flares in cSLE. Also, urinary NGAL levels do not change significantly prior to persistently active, inactive or improving global disease.

While the present invention has been illustrated in considerable detail by the description of embodiments thereof, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. A method for diagnosing and treating active lupus nephritis (LN) in a mammalian subject diagnosed with systemic lupus erythematosus (SLE), the method comprising the steps of:
   a) obtaining a sample from said mammalian subject;
   b) contacting said sample from said subject with a composition comprising an antibody capable of detecting transferrin (Tf) protein, an antibody capable of detecting ceruloplasmin (Cp) protein, an antibody capable of detecting alpha-1-acid-glycoprotein (AGP) protein, an antibody capable of detecting lipocalin-type prostaglandin-D synthetase (L-PGDS) protein, and an antibody capable of detecting neutrophil gelatinase associated lipocalin (NGAL) protein, wherein each said antibody comprises a detectable label;
   c) quantifying a quantity of one or more proteins detected in step (b);
   d) diagnosing said mammalian subject with active LN if the quantity of the proteins detected in step (b) is elevated above a predetermined cutoff value for the detected proteins of active LN; and
   d) administering an effective amount of an LN treatment to said diagnosed patient.

2. The method according to claim 1, wherein the predetermined cutoff values for the detected proteins of LN are as follows: urinary transferrin of >0.1 mg/dl, or >0.5 mg/dl, or >1 mg/dl; urinary ceruloplasmin of >500 ng/ml, or >600 ng/ml; urinary acid glycoprotein of >4,000 ng/ml, or >6,000 ng/ml, or >8,000 ng/ml, or >10,000 ng/ml; and urinary L-PGDS of >0.2 mg/di, or >0.3 mg/dl.

3. The method according to claim 1, wherein the sample is a urine sample, and the detected level of NGAL is higher than a predetermined level of NGAL in urine from normal, healthy subjects, by an amount of at least 5 ng/ml urine, or at least 10 ng/ml urine, or at least 15 ng/ml urine.

4. The method according to claim 1, wherein the level of NGAL is at least 50% higher than the predetermined level of NGAL in the urine of normal, healthy subjects, or at least 100% higher, or at least 150% higher, or at least 200% higher, or at least 300% higher.

5. The method according to claim 1 for diagnosing active lupus nephritis (LN), for further determining that the mammalian subject having active LN is likely to experience a renal flare, comprising the steps of: c) performing an assay on a urine sample, obtained from a mammalian subject diagnosed with active LN, that detects a level of neutrophil gelatinase-associated lipocalin (NGAL); and d) correlating an elevated level of NGAL to the mammalian subject being likely to experience a renal flare.

6. The method of claim 5 wherein the elevated level of NGAL is of at least 15 mg NGAL/ml urine, or at least 20 mg NGAL/ml urine, or at least 25 mg NGAL/ml urine, or at least 30 mg NGAL/ml urine, or at least 35 mg NGAL/ml urine, or at least 40 mg NGAL/ml urine.

7. The method of claim 5, wherein the onset of the renal flare occurs within the following 6 months, or within the following 5 months, or within the following 4 months, or within the following 3 months, or within the following 2 months, or within the following 1 month, or within the following 4 weeks, or within the following 3 weeks, or within the following 2 weeks.

8. The method according to claim 1 wherein the method is performed prior to a clinical diagnosis of LN of the mammalian subject diagnosed with SLE.

9. The method of claim 1, wherein said detection step comprises detection of at least two biomarkers.

* * * * *